(12) United States Patent
Blacker et al.

(10) Patent No.: US 7,250,526 B2
(45) Date of Patent: *Jul. 31, 2007

(54) TRANSFER HYDROGENATION PROCESS AND CATALYST

(75) Inventors: Andrew John Blacker, Huddersfield (GB); Christian Bubert, Bath (GB); Jonathan Michael Jeremy Williams, Bath (GB); Stephen Martin Brown, Huddersfield (GB)

(73) Assignee: NPIL Pharmaceuticals (UK) Limited, West Yorkshire (GB)

( * ) Notice: Subject to any disclaimer, the term of this patent is extended or adjusted under 35 U.S.C. 154(b) by 658 days.

This patent is subject to a terminal disclaimer.

(21) Appl. No.: 10/433,351

(22) PCT Filed: Nov. 29, 2001

(86) PCT No.: PCT/GB01/05285

§ 371 (c)(1),
(2), (4) Date: Oct. 15, 2003

(87) PCT Pub. No.: WO02/44111

PCT Pub. Date: Jun. 6, 2002

(65) Prior Publication Data

US 2004/0102313 A1  May 27, 2004

(30) Foreign Application Priority Data

Dec. 1, 2000 (GB) .................................. 0029356.3

(51) Int. Cl.
- C07F 17/02 (2006.01)
- C07F 15/06 (2006.01)
- C07C 311/16 (2006.01)
- C07C 29/14 (2006.01)
- C07C 29/143 (2006.01)
- C07B 53/00 (2006.01)
- C07B 43/04 (2006.01)
- C07D 217/10 (2006.01)
- C07D 209/08 (2006.01)

(52) U.S. Cl. ................ 556/136; 502/152; 502/166; 502/167; 546/139; 546/144; 546/148; 546/150; 548/469; 548/490; 556/137; 556/138; 564/85; 564/248; 564/269; 564/271; 564/272; 564/273; 564/274; 564/275; 564/278; 564/279; 564/463; 568/61; 568/715; 568/814

(58) Field of Classification Search .................... None
See application file for complete search history.

(56) References Cited

U.S. PATENT DOCUMENTS

| 6,372,931 B1 | 4/2002 | Blacker et al. ............. 556/136 |
| 6,509,467 B1 | 1/2003 | Blacker et al. ............. 546/139 |
| 6,545,188 B2 | 4/2003 | Blacker et al. ............. 568/814 |

FOREIGN PATENT DOCUMENTS

| WO | WO 98/42643 | 10/1998 |
| WO | WO 00/18708 | 4/2000 |

OTHER PUBLICATIONS

Noyori et al, J. Chem. Soc. Chem. Commun., 233-234 (1996).
Noyori et al, J.A.C.S., 117:7562-7563 (1996).
Matsumura, Kazuhiko, et al, "Asymmetric Transfer Hydrogenation of α, β-Acetylenic Ketones", J. Am. Chem Soc. vol. 119, No. 37, 1997, p. 8738-8739.
Bubert, Christian, et al, "Synthesis of water-soluble aminosulfonamide ligands and their application in enantioselective transfer hydrogenation", Tetrahedron Letters, vol. 42, 2001, p. 4037-4039.
Thorpe, Tim, et al, "Efficient rhodium and iridium-catalysed asymmetric transfer hydrogenation using water-soluble amniosulfonamide ligands", Tetrahedron Letters, vol. 42, 2001, p. 4041-4043.

*Primary Examiner*—Brian Davis
(74) *Attorney, Agent, or Firm*—Morgan Lewis & Bockius LLP

(57) ABSTRACT

A catalytic transfer hydrogenation process is provided. The catalyst employed in the process is a metal hydrocarbyl complex which is coordinated to defined bidentate ligands substituted with at least one group selected from an optionally substituted sulphonated hydrocarbyl group, a sulphonated perhalogenated hydrocarbyl group, or an optionally substituted sulphonated heterocyclyl group. Preferred metals include rhodium, ruthenium and iridium. Preferred bidentate ligands are diamines and aminoalcohols, particularly those comprising chiral centres. The hydrogen donor is advantageously a secondary alcohol or a mixture of triethylamine and formic acid. The process can be employed to transfer hydrogenate ketones and imines, which are preferably prochiral. Catalysts for use in such a process are also provided.

48 Claims, No Drawings

TRANSFER HYDROGENATION PROCESS AND CATALYST

This is a 371 national phase filing based on PCT/GB01/05285, which was filed Nov. 29, 2001 and claims priority benefit of United Kingdom Application No. 00298356.3, filed Dec. 1, 2000.

The present invention relates to transfer hydrogenation and encompasses processes for transfer hydrogenation, e.g. for producing optically active compounds and catalysts for use in such processes.

Numerous catalysts (generally comprising a transition metal) are known for effecting transfer hydrogenation. The following disclosures are of relevance.

(1) Noyori et al; J.A.C.S., 1995, 117 7562–7563: which discloses that use of chloro-ruthenium-mesitylene-N-monotosyl-1,2-diphenylethlyenediamine as catalyst in the transfer hydrogenation of acetophenone to 1-phenylethanol by propan-2-ol gave up to a 95% yield of product having 97% entantiomeric excess. Similar results were obtained starting from other alkylaryl ketones.

(2) Noyori et al: J. Chem.Soc.Chem, Commun, 1996, 233–234: which discloses catalysts similar to those of (1) above but containing other alkylbenzene ligands and various beta-amino alcohols in place of diphenylethylenediamine. The preferred arene ligand was hexamethylbenzene.

(3) Our earlier WO98/42643 which discloses transfer hydrogenation catalysts incorporating an optionally substituted cyclopentadienyl group co-ordinated or otherwise bonded to a metal (e.g. ruthenium, rhodium or iridium) capable of catalysing transfer hydrogenation. The hydrogenation of compound containing carbon-carbon, carbon-nitrogen, carbon-oxygen and carbon-sulphur double bonds is disclosed.

(4) Our earlier WO00/18708 discloses transfer hydrogenation of iminium salts (including protanated imine salts and quaternary imine salts) using catalysts of the type disclosed in (1) to (3).

The catalysts used in (1)–(4) whilst being effective for transfer hydrogenation have the disadvantage that they are difficult to recover from the product mixture.

This gives rise to a number of problems. Firstly, the catalysts are relatively expensive and the fact that at least a portion of the catalysts may not be recoverable adds to the expense of the hydrogenation process. Secondly, the fact that catalyst is present in the final product may prevent application of the hydrogenation process to the production of pharmaceutical and veterinary products since administration of the catalyst residue to humans or animals is undesirable.

It is therefore an object of the present invention to obviate or mitigate the abovementioned disadvantage.

According to a first aspect of the present invention there is provided a process for the transfer hydrogenation of an organic compound having a carbon-carbon or carbon-heteroatom double bond, said process comprising reacting said organic compound with a hydrogen donor in the presence of a catalyst having the general formula:

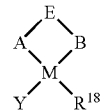

in which:

$R^{18}$ represents an optionally substituted hydrocarbyl or perhalogenated hydrocarbyl ligand;

A represents $-NR^{19}-$, $-NR^{20}-$, $-NHR^{19}$, $-NR^{19}R^{20}$ or $-NR^{20}R^{21}$ where $R^{19}$ is H, $C(O)R^{21}$, $SO_2R^{21}$, $C(O)NR^{21}R^{25}$, $C(S)NR^{21}R^{25}$, $C(=NR^{25})SR^{26}$ or $C(=NR^{25})OR^{26}$, $R^{20}$ and $R^{21}$ each independently represents an optionally substituted hydrocarbyl, perhalogenated hydrocarbyl or an optionally substituted heterocyclyl group, and $R^{25}$ and $R^{26}$ are each independently hydrogen or a group as defined for $R^{21}$;

B represents $-O-$, $-OH$, $OR^{22}$, $-S-$, $-SH$, $SR^{22}$, $-NR^{22}-$, $-NR^{23}-$, $-NHR^{23}$, $-NR^{22}R^{23}$, $-NR^{22}R^{24}$, $-PR^{22}-$ or $-PR^{22}R^{24}$ where $R^{23}$ is H, $C(O)R^{24}$, $SO_2R^{24}$, $C(O)NR^{24}R^{27}$, $C(S)NR^{24}R^{27}$, $C(=NR^{27})SR^{28}$ or $C(=NR^{27})OR^{28}$, $R^{22}$ and $R^{24}$ each independently represents an optionally substituted hydrocarbyl, perhalogenated hydrocarbyl or an optionally substituted heterocyclyl group, and $R^{27}$ and $R^{28}$ are each independently hydrogen or a group as defined for $R^{24}$;

E represents a linking group;

M represents a metal capable of catalysing transfer hydrogenation; and

Y represents an anionic group, a basic ligand or a vacant site;

provided that when Y is not a vacant site that at least one of A or B carries a hydrogen atom, characterised in that at least one of said groups $R^{20}$ to $R^{22}$ or $R^{24}$ to $R^{28}$ is present in the form of an optionally substituted sulphonated hydrocarbyl group, a sulphonated perhalogenated hydrocarbyl group, or an optionally substituted sulphonated heterocyclyl group.

According to a second aspect of the present invention there is provided catalysts as defined in the preceding paragraph.

As used herein (and unless the context otherwise requires) the term "sulphonated" is intended to cover the presence of the sulphonic acid moiety ($-SO_3H$) and salts thereof. Alkali metal (particularly sodium and potassium) sulphonates are preferred examples of sulphonate groups. Furthermore the enhanced solubility of the ligands (as provided by the polar sulphonate group) gives rise to the possibility of conducting hydrogenation reactions in water, other polar solvents, biphasic systems and in support polar phase catalysis. Alternatively, the sulphonate group may be present in the form of an anhydride (e.g. partially derived from a $CO_2H$ group).

The catalytic species is believed to be substantially as represented in the above formula. It may be introduced on a solid support.

The transfer hydrogenation process may for example be conducted as a homogenous reaction of the type disclosed in (1) to (4) above and the hydrogenated product obtained by standard make-up procedures such as extracting the product mixture with water (e.g. after dilution of the mixture with diethyl ether) and then drying the organic layer over, for example, magnesium sulphate followed by filtration and evaporation of solvent.

The presence of the polar sulphonate group does however give rise to the possibility of effecting the reaction and/or product recovery in various ways.

Thus, for example, at the end of the reaction there may be added to the product mixture an ion exchange resin so that the catalyst becomes immobilised on the resin by virtue of its sulphonate group. The product mixture may then be decanted from the resin and the product recovered with minimal or no catalyst residue. Accordingly, a further aspect of the present invention comprises a process of the first aspect of the present invention, further comprising an additional step of adding an ion exchange resin after reacting the organic compound with the hydrogen donor in the presence of the catalyst.

Alternatively the catalyst may be used as a "supported liquid phase catalyst" which comprises a support (e.g. beads) coated with a thin film of the catalyst dissolved in water or other polar solvent. The transfer hydrogenation phase is then effected by providing the support in the bulk organic phase (containing the hydrogen donor and the substrate to be hydrogenated) of the reaction. The base that is normally required for the reaction may be provided in either the film on the beads or dissolved in the bulk organic phase. Hydrogenated product will be produced in the bulk organic phase which, at the end of the reaction, may be decanted from the solid phase for recovery of the product. This procedure has the advantage of ensuring no or minimal catalyst residue in the first product.

As stated above, the catalyst incorporates at least one group $R^{20}$ to $R^{22}$ or $R^{24}$ to $R^{28}$ which is an optionally substituted sulphonated hydrocarbyl, sulphonated perhalogenated hydrocarbyl or optionally substituted sulphonated heterocyclyl group. The catalyst may incorporate at least one further $R^{20}$ to $R^{22}$ or $R^{24}$ to $R^{28}$ group in the form of an optionally substituted hydrocarbyl, perhalogenated hydrocarbyl or optionally substituted heterocyclyl group where the substituent(s) if present is/are other than sulphonate group(s). For convenience in the following description reference will be made to the types of hydrocarbyl, perhalogenated hydrocarbyl and heterocyclyl groups which may be used for $R^{20}$ to $R^{22}$ or $R^{24}$ to $R^{28}$ (as well as groups $R^{1-17}$), it being understood that the sulphonated form of $R^{20}$ to $R^{22}$ or $R^{24}$ to $R^{28}$ may be a sulphonated form of the moieties described therefore.

The process of the invention effects hydrogenation of a carbon-carbon or carbon-heteroatom double bond in an organic compound. Examples of the heteroatoms that may form part of the double bond include oxygen, sulphur and nitrogen. Examples of organic compounds that may be hydrogenated by the process of the invention are of formula I:

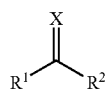

(1)

wherein:

X represents O, S, $CR^3R^4$, $NR^5$, $(NR^6R^7)^+Q^-$, $N^+R^8$—O$^-$, $(NR^9OR^{10})^{30}Q^-$, $NNR^{12}R^{13}$, $NNR^{12}SO_2R^{16}$, $NNR^{12}COR^{17}$, $(NR^{11}NR^{12}R^{13})^+Q^-$, $(NR^{11}NR^{12}C(=NR^{14})R^{15})^+Q^-$, $(NR^{11}NR^{12}SO_2R^{16})^+Q^-$, $(NR^{11}NR^{12}COR^{17})^+Q^-$, $NP(O)R^{15}R^{16}$, $NS(O)R^{15}$ or $NSO_2R^{15}$.

$Q^{31}$ represents a monovalent anion;

$R^1$, $R^2$, $R^3$, $R^4$, $R^5$, $R^6$, $R^7$, $R^8$, $R^9$, $R^{10}$, $R^{11}$ $R^{12}$, $R^{13}$ and $R^{14}$ each independently represents a hydrogen atom, an optionally substituted hydrocarbyl, a perhalogenated hydrocarbyl or an optionally substituted heterocyclyl group, one or more of $R^1$ and $R^2$, $R^1$ and $R^3$, $R^1$ and $R^5$, $R^1$ and $R^6$, $R^1$ and $R^8$, $R^1$ and $R^9$, $R^1$ and $R^{11}$, $R^1$ and $R^{12}$, $R^2$ and $R^4$, $R^2$ and $R^7$, $R^2$ and $R^{10}$, $R^3$ and $R^4$, $R^6$ and $R^7$, $R^9$ and $R^{10}$, $R^{11}$ and $R^{12}$, and $R^{12}$ and $R^{13}$ optionally being linked in such a way as to form an optionally substituted ring(s); and $R^{15}$, $R^{16}$ and $R^{17}$ each independently represents an optionally substituted hydrocarbyl, a perhalogenated hydrocarbyl or an optionally substituted heterocyclyl group;

Hydrocarbyl groups which may be represented by $R^{1-17}$, $R^{20-22}$ and $R^{24-28}$ independently include alkyl, alkenyl and aryl groups, and any combination thereof, such as aralkyl and alkaryl, for example benzyl groups.

Alkyl groups which may be represented by $R^{1-17}$, $R^{20-22}$ and $R^{24-28}$ include linear and branched alkyl groups comprising up to 20 carbon atoms, particularly from 1 to 7 carbon atoms and preferably from 1 to 5 carbon atoms. When the alkyl groups are branched, the groups often comprise up to 10 branched chain carbon atoms, preferably up to 4 branched chain atoms. In certain embodiments, the alkyl group may be cyclic, commonly comprising from 3 to 10 carbon atoms in the largest ring and optionally featuring one or more bridging rings. Examples of alkyl groups which may be represented by $R^{1-17}$, $R^{20-22}$ and $R^{24-28}$ include methyl, ethyl, propyl, 2-propyl, butyl, 2-butyl, t-butyl and cyclohexyl groups.

Alkenyl groups which may be represented by $R^{1-17}$, $R^{20-22}$ and $R^{24-28}$ include $C_{2-20}$, and preferably $C_{2-6}$ alkenyl groups. One or more carbon-carbon double bonds may be present. The alkenyl group may carry one or more substituents, particularly phenyl substituents. Examples of alkenyl groups include vinyl, styryl and indenyl groups. When either of $R^1$ or $R^2$ represents an alkenyl group, a carbon-carbon double bond is preferably located at the position β to the C=X moiety. When either of $R^1$ or $R^2$ represents an alkenyl group, the compound of formula (1) is preferably an α,β-unsaturated iminium compound.

Aryl groups which may be represented by $R^{1-17}$, $R^{20-22}$ and $R^{24-28}$ may contain 1 ring or 2 or more fused rings which may include cycloalkyl, aryl or heterocyclic rings. Examples of aryl groups which may be represented by $R^{1-17}$, $R^{20-22}$ and $R^{24-28}$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by $R^{1-17}$, $R^{20-22}$ and $R^{24-28}$ independently include perhalogenated alkyl and aryl groups, and any combination thereof, such as aralkyl and alkaryl groups. Examples of perhalogenated alkyl groups which may be represented by $R^{1-17}$, $R^{20-22}$ and $R^{24-28}$ include —$CF_3$ and —$C_2F_5$.

Heterocyclic groups which may be represented by $R^{1-17}$, $R^{20-22}$ and $R^{24-28}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. When either of $R^1$ or $R^2$ represents or comprises a heterocyclic group, the atom in $R^1$ or $R^2$ bonded to the C=X group is preferably a carbon atom. Examples of heterocyclic groups which may be represented by $R^{1-17}$, $R^{20-22}$ and $R^{24-28}$ include pyridyl, pyrimidyl, pyrrolyl, thiophenyl, furanyl, indolyl, quinolyl, isoquinolyl, imidazoyl and triazoyl groups.

When any of $R^{1-17}$, $R^{20-22}$ and $R^{24-28}$ is a substituted hydrocarbyl or heterocyclic group, the substituent(s) should be such so as not to adversely affect the rate or stereoselectivity of the reaction. Optional substituents include halogen, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for $R^1$ above. One or more substituents may be present.

When any of $R^1$ and $R^2$, $R^1$ and $R^3$, $R^1$ and $R^5$, $R^1$ and $R^6$, $R^1$ and $R^8$, $R^1$ and $R^9$, $R^1$ and $R^{11}$, $R^1$ and $R^{12}$, $R^2$ and $R^4$, $R^2$ and $R^7$, $R^2$ and $R^{10}$, $R^3$ and $R^4$, $R^6$ and $R^7$, $R^9$ and $R^{10}$, $R^{11}$ and $R^{12}$, and $R^{12}$ and $R^{13}$ are linked in such a way that when taken together with either the carbon atom and/or atom X of the compound of formula (1) that a ring is formed, it is preferred that these be 5, 6 or 7 membered rings. The rings formed in this way may additionally be fused to each other or to other ring systems. Examples of rings which may be so formed include:

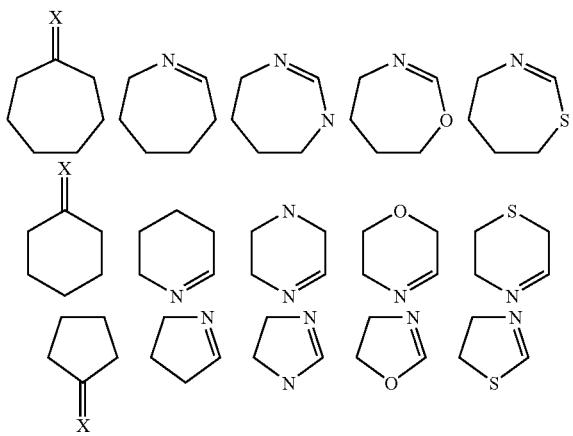

wherein X is as defined above and the rings may be optionally substituted or may be fused to other rings.

In certain preferred embodiments, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are all independently $C_{1-6}$ alkyl or are a combination of aryl, particularly phenyl, $C_{1-6}$ alkyl and $C_{6-10}$aralkyl. Substituents may be present, particularly substituents para to the C=X group when one or more of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ is a phenyl group.

In especially preferred embodiments, $R^4$, $R^5$, $R^6$, or $R^8$ are $C_{1-6}$ alkyl or $C_{6-10}$aralkyl, especially methyl, benzyl or PhCHCH$_3$.

Compounds of formula (1) where X is represented by NR$^5$ or (NR$^6$R$^7$)$^+$Q$^-$, include imines or iminium salts. Where a compound of formula (1) is an imine, it may optionally be converted to an iminium salt. Iminium salts are preferred over imines. Preferred iminium salts are represented by compounds of formula (1) in which X is (NR$^6$R$^7$)$^+$Q$^-$ such that either R$^6$ or R$^7$ are hydrogen but that R$^6$ and R$^7$ are not identical. When the compound of formula (1) is an iminium salt, an anion represented by Q$^-$ is present.

Anions which may be represented by Q$^-$ include halides, optionally substituted arylsulphonates, such as optionally substituted phenyl and napthyl sulphonates, optionally substituted alkylsulphonates including halogenated alkylsulphonates, such as $C_{1-20}$ alkylsulphonates, optionally substituted carboxylates, such as $C_{1-10}$ alkyl and aryl carboxylates, ions derived from the polyhalogenation of boron, phosphorous or antimony, and other common inorganic ions for example perchlorate. Examples of anions which may be present are bromide, chloride, iodide, hydrogen sulphate, tosylate, formate, acetate, tetrafluoroborate, hexafluorophosphate, hexafluoroantimonate, perchlorate, trifluoromethanesulphonate and trifluoroacetate. Preferred anions include bromide, chloride, iodide, formate and trifluoroacetate, particularly preferred anions include iodide, formate and trifluoroacetate.

In certain preferred embodiments, X is a group of formula (NR$^6$R$^7$)$^+$Q$^-$ and R$^1$ and R$^6$ are linked in such a way that when taken together with the carbon atom and the nitrogen atom of the C=X group of the compound of formula (1) that a 5, 6 or 7 membered ring is formed, R$^7$ is $C_{1-6}$ alkyl or $C_{6-10}$aralkyl, especially methyl, benzyl or PhCHCH$_3$, and R$^2$ is optionally substituted hydrocarbyl, preferably $C_{1-6}$ alkyl, or optionally substituted phenyl especially methoxy, hydroxy or fluoro substituted phenyl. The 5, 6 or 7 membered ring formed by linking R$^1$ and R$^6$ optionally may be fused to another ring system, preferably a benzenoid system which may be substituted, preferred substituents include hydroxy, methoxy and fluoro.

In certain preferred embodiments X is O so that the compound of the formula (I) is a ketone.

Most advantageously, the compound of formula (1) is prochiral, such that the hydrogenated product comprises a chiral atom to which R$^1$, R$^2$ and X are each bonded. Such an asymmetric transfer hydrogenation process forms an especially preferred aspect of the present invention. Most commonly, when the compound of formula (1) is prochiral, R$^1$ and R$^2$ are different, and neither is hydrogen. Advantageously, one of R$^1$ and R$^2$ is aliphatic and the other is aryl or heterocyclyl.

Examples of compounds of formula (1) include acetophenone, 4-chloroacetophenone, 4-methoxyacetophenone, 4-trifluoromethylacetophenone, 4-nitroacetophenone, 2-chloroacetophenone and acetophenone benzylimine.

Further examples of compounds of formula (1) include:

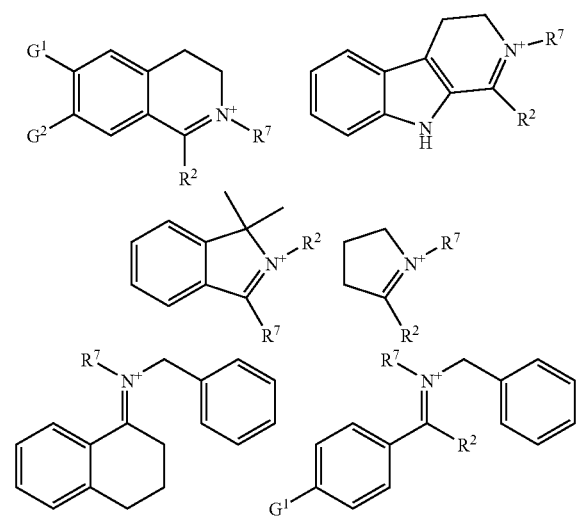

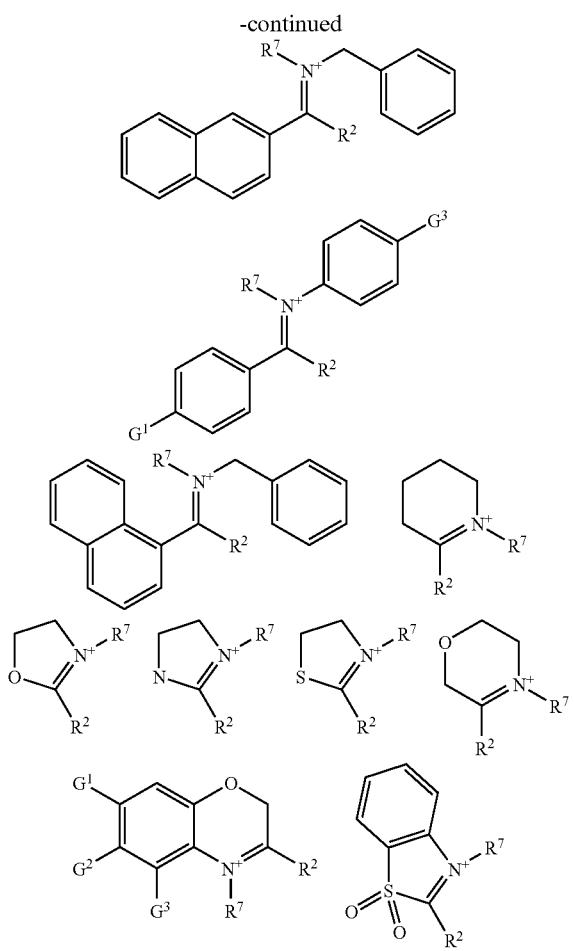

wherein $R^2$ and $R^7$ are as described above and $G^1$, $G^2$ and $G^3$ are independently hydrogen, chloro, bromo, fluoro, iodo, cyano, nitro, hydroxy, amino, thiol, acyl, hydrocarbyl, perhalogenated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for $R^1$ above.

Hydrogen donors include hydrogen, primary and secondary alcohols, primary and secondary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, secondary alcohols are preferred, especially propan-2-ol and butan-2-ol.

Primary and secondary amines which may be employed as hydrogen donors comprise commonly from 1 to 20 carbon atoms, preferably from 2 to 14 carbon atoms, and more preferably 3 or 8 carbon atoms. Examples of primary and secondary amines which may be represented as hydrogen donors include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine and piperidine. When the hydrogen donor is an amine, primary amines are preferred, especially primary amines comprising a secondary alkyl group, particularly isopropylamine and isobutylamine.

Carboxylic acids or their esters which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids which may be employed as hydrogen donors include formic acid, lactic acid, ascorbic acid and mandelic acid. The most preferred carboxylic acid is formic acid. In certain preferred embodiments, when a carboxylic acid is employed as hydrogen donor, at least some of the carboxylic acid is preferably present as salt, preferably an amine, ammonium or metal salt. Preferably, when a metal salt is present the metal is selected from the alkali or alkaline earth metals of the periodic table, and more preferably is selected from the group I elements, such as lithium, sodium or potassium. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the mole ratio of acid to amine is between 1:1 and 50:1 and preferably between 1:1 and 10:1, and most preferably about 5:2. When at least some of the carboxylic acid is present as a metal salt, particularly when a mixture of formic acid and a group I metal salt is employed, the mole ratio of acid to metal ions present is between 1:1 and 50:1 and preferably between 1:1 and 10:1, and most preferably about 2:1. The ratios of acid to salts may be maintained during the course of the reaction by the addition of either component, but usually by the addition of the carboxylic acid.

Readily dehydrogenatable hydrocarbons which may be employed as hydrogen donors comprise hydrocarbons which have a propensity to aromatise or hydrocarbons which have a propensity to form highly conjugated systems. Examples of readily dehydrogenatable hydrocarbons which may be employed by as hydrogen donors include cyclohexadiene, cyclohexene, tetralin, dihydrofuran and terpenes.

Clean reducing agents which may be represented as hydrogen donors comprise reducing agents with a high reduction potential, particularly those having a reduction potential relative to the standard hydrogen electrode of greater than about −0.1 eV, often greater than about −0.5 eV, and preferably greater than about −1 eV. Examples of clean reducing agents which may be represented as hydrogen donors include hydrazine and hydroxylamine.

The most preferred hydrogen donors are propan-2-ol, butan-2-ol, triethylammonium formate and a mixture of triethylammonium formate and formic acid. However, in certain embodiments when the compound of Formula (1) is a protonated imminium salt, it may be desirable to employ a hydrogen donor which is not a carboxylic acid or a salt thereof.

The optionally substituted hydrocarbyl or perhalogenated hydrocarbyl ligand which may be represented by $R^{18}$ includes optionally substituted aryl, alkenyl and cyclopentadienyl ligands.

Optionally substituted aryl ligands which may be represented by $R^{18}$ may contain 1 ring or 2 or more fused rings which include cycloalkyl, aryl or heterocyclic rings. The ligand may comprise a 6 membered aromatic ring. The ring or rings of the aryl ligand are often substituted with hydrocarbyl groups. The substitution pattern and the number of substituents will vary and may be influenced by the number of rings present, but often from 1 to 6 hydrocarbyl substituent groups are present, preferably 2, 3 or 6 hydrocarbyl groups and more preferably 6 hydrocarbyl groups. Preferred hydrocarbyl substituents include methyl, ethyl, iso-propyl, menthyl, neomenthyl and phenyl. Particularly when the aryl ligand is a single ring, the ligand is preferably benzene or a substituted benzene. When the ligand is a perhalogenated hydrocarbyl, preferably it is a polyhalogenated benzene such as hexachlorobenzene or hexafluorobenzne. When the hydrocarbyl substituents contain enantiomeric and/or diastereomeric centres, it is preferred that the enantiomerically and/or diastereomerically purified forms of these are used. Benzene, p-cymyl, mesitylene and hexamethylbenzene are especially preferred ligands having a 6 membered aromatic ring.

Optionally substituted alkenyl ligands which may be represented by $R^{18}$ include $C_{2-30}$, and preferably $C_{5-12}$, alkenes or cycloalkenes with preferably two or more carbon-carbon double bonds, preferably only two carbon-carbon double bonds. The carbon-carbon double bonds may optionally be conjugated to other unsaturated systems which may be present, but are preferably conjugated to each other. The alkenes or cycloalkenes may be substituted preferably with hydrocarbyl substituents. When the alkene has only one double bond, the optionally substituted alkenyl ligand may comprise two separate alkenes. Preferred hydrocarbyl substituents include methyl, ethyl, iso-propyl and phenyl. Examples of optionally substituted alkenyl ligands include cyclo-octa-1,5-diene and 2,5-norbornadiene.

It is however particularly preferred that $R^{18}$ is an optionally substituted cyclopentadienyl group.

Optionally substituted cyclopentadienyl group which may be represented by $R^{18}$ include particularly ones capable of eta-5 bonding. The cyclopentadienyl group is often substituted with from 1 to 5 hydrocarbyl groups, preferably with 3 to 5 hydrocarbyl groups and more preferably with 5 hydrocarbyl groups. Preferred hydrocarbyl substituents include methyl, ethyl and phenyl. When the hydrocarbyl substituents contain enantiomeric and/or diastereomeric centres, it is preferred that the enantiomerically and/or diastereomerically purified forms of these are used. Examples of optionally substituted cyclopentadienyl groups include cyclopentadienyl, pentamethyl-cyclopentadienyl, pentaphenylcyclopentadienyl, tetraphenylcyclopentadienyl, ethyltetramethylpentadienyl, menthyltetraphenylcyclopentadienyl, neomenthyl-tetraphenylcyclopentadienyl, menthylcyclopentadienyl, neomenthylcyclopentadienyl, tetrahydroindenyl, menthyltetrahydroindenyl and neomenthyltetrahydroindenyl groups. Pentamethylcyclopentadienyl is especially preferred.

It is particularly preferred that $R^{18}$ is an optionally substituted cyclopentadienyl group.

When either A or B is an amide group represented by $-NR^{19}-$, $-NHR^{19}$, $NR^{19}R^{20}$, $-NR^{23}-$, $-NHR^{23}$ or $NR^{22}R^{23}$ wherein $R^{20}$ and $R^{21}$ are as hereinbefore defined, and where $R^{19}$ or $R^{23}$ is an acyl group represented by $-C(O)R^{21}$ or $-C(O)R^{24}$, $R^{21}$ and $R^{24}$ independently are often linear or branched sulphonated $C_{1-7}$alkyl, sulphonated $C_{1-8}$-cycloalkyl or sulphonated aryl, for example sulphonated phenyl. Examples of sulphonated acyl groups which may be represented by $R^{19}$ or $R^{23}$ include sulphonated benzoyl, acetyl and halogenoacetyl groups.

When either A or B is present as a sulphonamide group represented by $-NR^{19}-$, $-NHR^{19}$, $NR^{19}R^{20}$, $-NR^{23}-$, $-NHR^{23}$ or $NR^{22}R^{23}$ wherein $R^{20}$ and $R^{22}$ are as hereinbefore defined, and where $R^{19}$ or $R^{23}$ is a sulphonyl group represented by $-S(O)_2R^{21}$ or $-S(O)_2R^{24}$, $R^{21}$ and $R^{24}$ independently are often linear or branched sulphonated $C_{1-8}$alkyl, sulphonated $C_{1-8}$cycloalkyl or sulphonated aryl, for example sulphonated phenyl. Preferred sulphonyl groups include sulphoanted derivatives of methanesulphonyl, trifluoromethanesulphonyl and especially phenylsulphonyl groups and naphthylsulphonyl groups.

When either of A or B is present as a group represented by $-NR^{19}-$, $-NHR^{19}$, $NR^{19}R^{20}$, $-NR^{23}-$, $-NHR^{23}$ or $NR^{22}R^{24}$ wherein $R^{20}$ and $R^{23}$ are as hereinbefore defined, and where $R^{19}$ or $R^{23}$ is a group represented by $C(O)NR^{21}R^{25}$, $C(S)NR^{21}R^{25}$, $C(=NR^{25})SR^{26}$, $C(=NR^{25})OR^{26}$, $C(O)NR^{24}R^{27}$, $C(S)NR^{24}R^{27}$, $C(=NR^{27})SR^{28}$ or $C(=NR^{27})OR^{28}$, $R^{21}$ and $R^{24}$ independently are often linear or branched sulphonated $C_{1-8}$alkyl, such as methyl, ethyl, isopropyl, $C_{1-8}$cycloalkyl or sulphonated aryl, for example phenyl, groups and $R^{22-25}$ are often each independently hydrogen or linear or branched $C_{1-8}$alkyl, such as methyl, ethyl, isopropyl, sulphonated $C_{1-8}$cycloalkyl or aryl, for example phenyl, groups.

When B is present as a group represented by $-OR^{22}$, $-SR^{22}$, $-PR^{22}-$ or $-PR^{22}R^{24}$, $R^{22}$ and $R^{24}$ independently are often linear or branched $C_{1-8}$alkyl, such as methyl, ethyl, isopropyl, $C_{1-8}$cycloalkyl or aryl, for example phenyl.

It will be recognised that the precise nature of A and B will be determined by whether A and/or B are formally bonded to the metal or are coordinated to the metal via a lone pair of electrons.

It is particularly preferred in accordance with the invention that A is a group of the formula $-NHR^{19}$ or $-NR^{19}-$ where $R^{19}$ is represented by the group $-SO_2R^{21}$ in which $R^{21}$ is an optionally substituted sulphonated hydrocarbyl group, sulphonated perhalogenated hydrocarbyl group or optionally substituted sulphonated heterocyclyl group. Most preferably $R^{21}$ is a sulphonated phenyl group having n sulphonate groups where n is 1 to 5. When n is 1 to 4 the sulphonate groups may be present in any substitution pattern on the aromatic ring. In the particular case where n=1 then the sulphonate group may be ortho, meta or para to the sulphonamide group.

B is preferably $-NH_2$ or $-NH-$.

The groups A and B are connected by a linking group E. The linking group E achieves a suitable conformation of A and B so as to allow both A and B to bond or coordinate to the metal, M. A and B are commonly linked through 2, 3 or 4 atoms. The atoms in E linking A and B may carry one or more substituents. The atoms in E, especially the atoms alpha to A or B, may be linked to A and B, in such a way as to form a heterocyclic ring, preferably a saturated ring, and particularly a 5, 6 or 7-membered ring. Such a ring may be fused to one or more other rings. Often the atoms linking A and B will be carbon atoms. Preferably, one or more of the carbon atoms linking A and B will carry substituents in addition to A or B. Substituent groups include those which may substitute $R^1$, as defined above. Advantageously, any such substituent groups are selected to be groups which do not coordinate with the metal, M. Preferred substituents include halogen, cyano, nitro, sulphonyl, hydrocarbyl, perhalogenated hydrocarbyl and heterocyclyl groups as defined above. Most preferred substituents are $C_{1-6}$ alkyl groups, and phenyl groups. Most preferably, A and B are linked by two carbon atoms, and especially an optionally substituted ethyl moiety. When A and B are linked by two carbon atoms, the two carbon atoms linking A and B may comprise part of an aromatic or aliphatic cyclic group, particularly a 5, 6 or 7-membered ring. Such a ring may be fused to one or more other such rings. Particularly preferred are embodiments in which E represents a 2 carbon atom separation and one or both of the carbon atoms carries an optionally substituted aryl group as defined above or E represents a 2 carbon atom separation which comprises a cyclopentane or cyclohexane ring, optionally fused to a phenyl ring.

E preferably comprises part of a compound having at least one stereospecific centre. Where any or all of the 2, 3 or 4 atoms linking A and B are substituted so as to define at least one stereospecific centre on one or more of these atoms, it is preferred that at least one of the stereospecific centres be located at the atom adjacent to either group A or B. When at least one such stereospecific centre is present, it is advantageously present in an enantiomerically purified state.

When B represents —O— or —OH, and the adjacent atom in E is carbon, it is preferred that B does not form part of a carboxylic group.

Sulphonated compounds which may be represented by A—E—B, or from which A—E—B may be derived by deprotonation, are often aminoalcohols or diamines in which an or the amino nitrogen atom has bound (directly or indirectly) thereto a substituent incorporating a group $R^{20}$ to $R^{22}$ or $R^{24}$ to $R^{28}$ in the form of an optionally substituted sulphonated hydrocarbyl group, a sulphonated perhalogenated hydrocarbyl group or an optionally substituted sulphonated heterocyclyl group. Examples of aminoalcohols from which said N-substituted compound may be derived including 4-aminoalkan-1-ols, 1-aminoalkan-4-ols, 3-aminoalkan-1-ols, 1-aminoalkan-3-ols, and especially 2-aminoalkan-1-ols, 1-aminoalkan-2-ols, 3-aminoalkan-2-ols and 2-aminoalkan-3-ols, and particularly 2-aminoethanols or 3-aminopropanols. Further aminoalcohols are 2-aminocyclopentanols and 2-aminocyclohexanols, preferably fused to a phenyl ring. Examples of diamines from which said N-substituted compounds may be derived include 1,4-diaminoalkanes, 1,3-diaminoalkanes, especially 1,2- or 2,3-diaminoalkanes and particularly ethylenediamines. Further diamines are 1,2-diaminocyclopentanes and 1,2-diaminocyclohexanes, preferably fused to a phenyl ring. The aminoalcohols or diamines are advantageously substituted, especially on the linking group, E, by at least one alkyl group, such as a $C_{1-4}$-alkyl, and particularly a methyl, group or at least one aryl group, particularly a phenyl group.

In summary it is particularly preferred that E has two carbon atoms linking A and B, one or both of these atoms being optionally substituted. In certain preferred embodiments E is of the formula —CHR$^{30}$—CHR$^{31}$— where $R^{30}$ and $R^{31}$ are independently hydrogen or an optionally substituted hydrocarbyl group.

In other preferred embodiments, E is a carbon-carbon bond that is part of an optionally substituted cycloaliphatic ring, preferably cyclopentyl or cyclohexyl.

Examples of ligands from which compounds A—E—B may be derived are as follows:

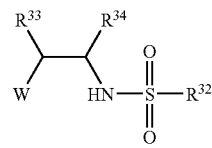

in which:

W is —OH or —NH$_2$;

$R^{32}$ is an aryl group having at least one —SO$_3$H or SO$_3$M$^1$ (M$^1$=alkali metal) substituent and is further optionally substituted, e.g. with a carboxylic acid group which may, for example, be ortho to the —SO$_3$H or —SO$_3$M$^1$ group and may lead to anhydride formulation therewith. More preferably $R^{32}$ is a phenyl group having one —SO$_3$H or —SO$_3$M$^1$ substituent; and $R^{33}$, $R^{34}$ are independently optionally substituted hydrocarbyl groups or $R^{33}$ and $R^{34}$ are optionally linked in such a way as to define an optionally substituted ring, more preferably $R^{33}$ and $R^{34}$ are independently phenyl or $R^{33}$ and $R^{34}$ are linked so as to define a cyclohexyl ring.

Specific examples of aminoalcohols and diamines from which the sulphonated compounds A—E—B may be derived are:

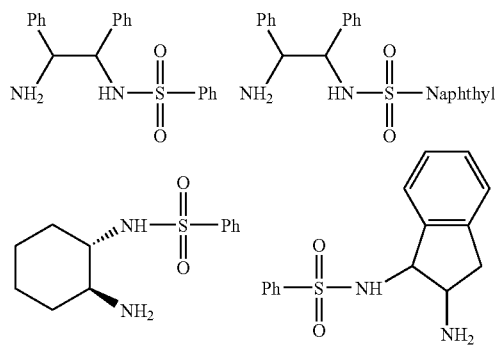

Advantageously, certain ligands are prepared by oxidative cleavage of the corresponding di-sulphide.

Accordingly there is provided a process comprising reacting a di-sulphide of formula:

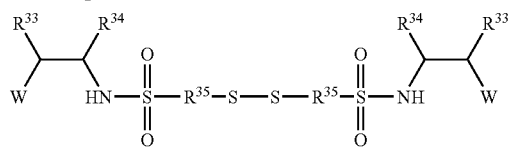

with an oxidant to produce a compound of formula:

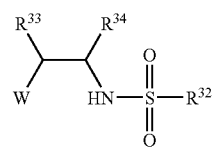

wherein:

W is —OH or —NH$_2$;

R$^{32}$ is an aryl group having at least one —SO$_3$H or SO$_3$M$^1$ (M$^1$=alkali metal) substituent;

R$^{35}$ is an aryl group; and

R$^{33}$, R$^{34}$ are independently optionally substituted hydrocarbyl groups or R$^{33}$ and R$^{34}$ are optionally linked in such a way as to define an optionally substituted ring, more preferably R$^{33}$ and R$^{34}$ are independently phenyl or R$^{33}$ and R$^{34}$ are linked so as to define a cyclohexyl ring.

Preferably the substitution pattern of the aryl group R$^{32}$ is such that the —SO$_3$H or SO$_3$M$^1$ (M$^1$=alkali metal) substituent is positioned para with respect to the SO$_2$NH—CHR$^{34}$—CHR$^{33}$—W group. Corresponding a similar substitution pattern in R$^{35}$ is preferred.

Preferably the oxidant is alkaline hydrogen peroxide, particularly a mixture is sodium hydroxide solution and hydrogen peroxide solution.

Metals which may be represented by M include metals which are capable of catalysing transfer hydrogenation. Preferred metals include transition metals, more preferably the metals in Group VIII of the Periodic Table, especially ruthenium, rhodium or iridium. When the metal is ruthenium it is preferably present in valence state II. When the metal is rhodium or iridium it is preferably present in valence state I.

Anionic groups which may be represented by Y include hydride, hydroxy, hydrocarbyloxy, hydrocarbylamino and halogen groups. Preferably when a halogen is represented by Y, the halogen is chloride. When a hydrocarbyloxy or hydrocarbylamino group is represented by Y, the group may be derived from the deprotonation of the hydrogen donor utilised in the reaction.

Basic ligands which may be represented by Y include water, C$_{1-4}$ alcohols, C$_{1-8}$ primary or secondary amines, or the hydrogen donor which is present in the reaction system. A preferred basic ligand represented by Y is water.

Most preferably, the nature of A—E—B, R$^{18}$ and Y are chosen such that the catalyst is chiral. When such is the case, an enantiomerically and/or diastereomerically purified form is preferably employed. Such catalysts are most advantageously employed in asymmetric transfer hydrogenation processes. In many embodiments, the chirality of the catalyst is derived from the nature of A—E—B.

The process is carried out preferably in the presence of a base, especially when Y is not a vacant site. The pK$_a$ of the base is preferably at least 8.0, especially at least 10.0. Convenient bases are the hydroxides, alkoxides and carbonates of alkali metals; tertiary amines and quaternary ammonium compounds. Preferred bases are sodium 2-propoxide and triethylamine. When the hydrogen donor is not an acid, the quantity of base used can be up to 5.0, commonly up to 3.0, often up to 2.5 and especially in the range 1.0 to 3.5, by moles of the catalyst. When the hydrogen donor is an acid, the catalyst may be contacted with a base prior to the introduction of the hydrogen donor. In such a case, the mole ratio of base to catalyst prior to the introduction of the hydrogen donor is often from 1:1 to 3:1, and preferably about 1:1.

Although gaseous hydrogen may be present, the process is normally operated in the absence of gaseous hydrogen since it appears to be unnecessary.

Advantageously, the process is carried out in the substantial absence of carbon dioxide.

When the product(s) from dehydrogenation of the hydrogen donor is volatile, for example boils at under 100° C., the removal of this volatile product is preferred. The removal can be accomplished by distillation preferably at less than atmospheric pressure or by use of inert gas sparging. When reduced pressure distillation is employed, the pressure is often no more than 500 mmHg, commonly no more than 200 mmHg, preferably in the range of from 5 to 100 mmHg, and most preferably from 10 to 80 mmHg. When the product(s) from dehydrogenation of the hydrogen donor is a gaseous material, for example when formic acid is present as a hydrogen donor, the removal is most preferably accomplished by the use of inert gas sparging, with for example nitrogen.

Suitably the process is carried out at temperatures in the range of from minus 78 to plus 150° C., preferably from minus 20 to plus 110° C. and more preferably from minus 5 to plus 60° C. The initial concentration of the substrate, a compound of formula (1), is suitably in the range 0.05 to 1.0 and, for convenient larger scale operation, can be for example up to 6.0 more especially 0.25 to 2.0, on a molar basis. The molar ratio of the substrate to catalyst is suitably no less than 50:1 and can be up to 50000:1, preferably between 100:1 and 5000:1 and more preferably between 200:1 and 2000:1. The hydrogen donor is preferably employed in a molar excess over the substrate, especially from 5 to 20 fold or, if convenience permits, greater, for example up to 500 fold. After reaction, the mixture is worked up by standard procedures.

During the reaction a solvent may be present, preferably a polar solvent, more preferably a polar aprotic solvent, for example acetonitrile, dimethylformamide or dichloromethane. Conveniently, the hydrogen donor may be the solvent when the hydrogen donor is liquid at the reaction temperature, or it may be used in combination with a diluent. Usually it is preferred to operate in substantial absence of water, but water does not appear to inhibit the reaction. If the hydrogen donor or the reaction solvent is not miscible with water and the desired product is water soluble, it may be desirable to have water present as a second phase extracting the product, pushing the equilibrium and preventing loss of product optical purity as the reaction proceeds. The concentration of substrate may be chosen to optimise reaction time, yield and enantiomeric excess.

The catalytic species is believed to be substantially as represented in the above formula. It may be employed as an oligomer or metathesis product, on a solid support or may be generated in situ.

The catalyst can be made by reacting a metal aryl or alkenyl halide complex with a compound of formula A—E—B as defined above or a protonated equivalent from which it may be derived, and, where Y represents a vacant site, reacting the product thereof with a base. The metal aryl or alkenyl halide complex preferably has the formula [MR$^{18}$Z$_2$]$_2$ when M is ruthenium (II) and has the formula [MR$^{18}$Z]$_2$ when M is iridium or rhodium (I), wherein R$^{18}$ is as defined above, and Z represents a halide, particularly chloride.

For the preparation of the catalysts according to the present invention, a solvent is preferably present. Suitable reaction temperatures are in the range 0–100° C., for example 20–70° C., often giving reaction times of 0.5–24.0 h. After reaction is complete, the catalyst may if desired be isolated, but is more conveniently stored as the solution or used soon after preparation. The solution can contain the hydrogen donor and this, if a secondary alcohol, may be present in or used as the solvent for step (a) and/or (b). The preparation and after-handling should preferably be under an inert atmosphere, and particularly in carbon dioxide and oxygen-free conditions.

The catalyst or catalyst solution is generally treated with base either just prior to use in a transfer hydrogenation reaction, or during use. This can be accomplished by adding base to the catalyst in solution, or to the compound of formula (1) in solution, or by addition to the transfer hydrogenation reaction. Iminium salts can generally be obtained by known literature methods, for example the quaternisation of imines, such as by treatment of imines with alkylating agents. Transfer hydrogenation can be accomplished by transferring the solution of catalyst to a solution of substrate, a compound of general formula I. Alternatively a solution of substrate can be added to a solution of catalyst. Base may be pre-added to the catalyst solution and/or the substrate solution, or can be added later. The hydrogen donor if not already present in the catalyst solution may be added to the substrate solution, or may be added to the reaction mixture.

The invention is illustrated by the following Examples.

The invention will be illustrated by the following non-limiting Examples. For convenience, the Examples are divided into two sections, viz a Ligand Synthesis Section in which Examples LS1–4 and LS18 describe the synthesis of various ligands embraced by the formula A—E—B described above and a "Catalyst Preparation and Hydrogenation" Section in which Examples TH5–17 and describe preparation of catalysts with ligands as synthesised in Examples LS1–4 and transfer hydrogenation reactions employing these catalysts. Example TH19 describes a transfer hydrogenation process wherein the catalyst is removed at he end of reaction by treatment with ion exchange resins.

EXAMPLES

Example LS 1

Preparation of Sodium (1S, 2S)-1,2-diphenylethylenediamine-N-phenylsulfonyl-4-sulfonate (CB 3.016)

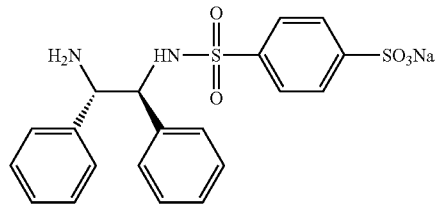

CB3.016

(i) Synthesis of Sodium 4,4'-dithiobisbenzenesulfonate. (CB3.011)

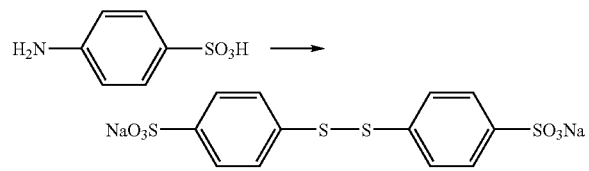

Sodium 4,4'-dithiobisbenzenesulfonate (CB3.011) was synthesised following the protocol of Smith et. al (H. A Smith, G. Goughty, G Dorin *j. Chem. Soc.*, 1964, 29, 1484–1488) with some minor modifications. Sulfanilic acid (47.5 g, 0.25 mol) and anhydrous sodium carbonate were dissolved in water (500 ml) by warming. The solution was cooled to 15° C. and sodium nitrite (18.5 g, 0.27 mol) in water (50 ml) was added. The mixture was poured slowly into conc. hydrochloric acid (52.5 ml, 0.64 mol) and crushed ice (300 g) and the resulting suspension was stirred for 15 minutes.

Sodium sulfide nonahydrate (65 g, 0.27 mol) and powdered sulfur (8.5 g, 0.27 mol) were dissolved in water (75 ml) at 100° C. A solution of sodium hydroxide (10 g, 0.25 mol) in water (100 ml) was added and the resulting disodium disulfide solution was cooled to 0° C. (ice bath). The diazo solution was added over a period of 30 minutes, along with 50 g of ice to keep the temperature below 5° C. The ice bath was removed and the reaction mixture was allowed to come to room temperature. After 2 hours the evolution of nitrogen ceased and the reaction mixture was acidified to pH 2 by addition of conc. hydrochloric acid. The precipitated sulfur was filtered off and the solution was concentrated by heating on a stirrer hotplate to a volume of ca. 500 ml. After cooling to r.t. the solution was neutralised with sodium hydroxide solution (10% in water) and concentrated to 400 ml. The product crystalised after standing overnight at r.t. and was collected in a buchner funnel and dried under high vacuum. Yield 19.8 g (37.5%, 46.9 mmol). $^1$H NMR (400 MHz, D$_2$O) d 7.36 (d, J=8.2 Hz, 4H), 7.53 (d, J=8.2 Hz, 4H); $^{13}$C NMR (100 MHz, D$^2$O) d 126.47 (+), 127.04 (+), 140.07 (C$_{quart}$), 141.38 (C$_{quart}$).

(ii) Synthesis of 4,4'-Disulfanediyl-bis-benzene sulfonyl chloride. (CB3.012)

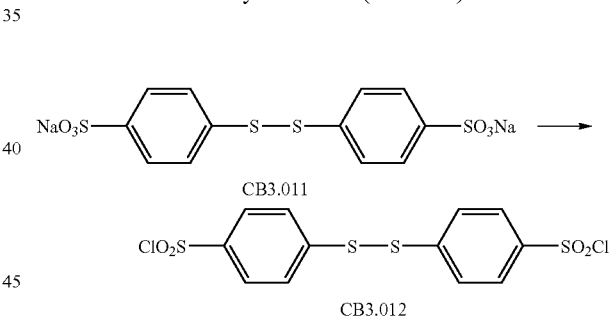

A flask (100 ml) with reflux condenser and a bubbler was charged with CB3.011 (10 g, 23.7 mmol), POCl$_3$ (10 ml) and PCl5 (5 g). The mixture was heated to reflux for 2 hours (120° C. oil bath temperature). After cooling to room temperature temperative dichloromethane (50 ml) was added and the resulting mixture was poured into ice. After 1 hour of intensive stirring the organic layer was separated and stirred with conc. bicarbonate solution (100 ml) for another hour. The organic layer was separated again, dried over sodium sulfate and concentrated to a volume of ca. 25 ml. The product was precipitated by slow addition of cyclohexane with stirring, filtered off and dried under high vacuum. Yield 6.89 g (16.6 mmol, 70%). m.p. 139° C. (Lit.$^{Ref1}$: 142° C.); $^1$H NMR (400 MHz, CDCl$_3$) d 7.69 (d, J=8.6 Hz, 4H), 7.98 (d, J=8.6 Hz, 4H); $^{13}$C NMR (100 MHz, CDCl$_3$) d 126.69 (+), 128.08 (+), 143.03 (C$_{quart}$), 145.05 (C$_{quart}$); MS (+FAB(3-NBA)) m/e 413.9 (100, M).

(Ref 1: T. Zincke, W. Frohneberg *Chem Ber.*, 1909, 42, 2721–2736)

(iii) Synthesis of (CB3.010)

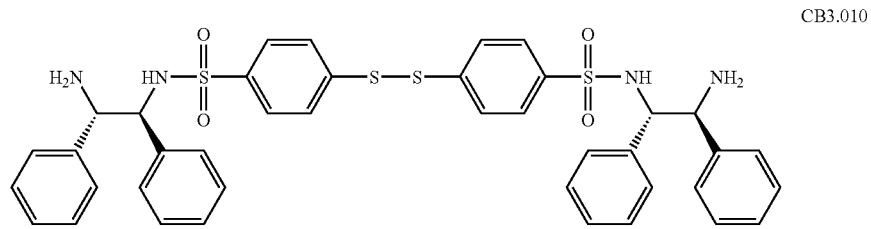

To a solution of (S,S)-diphenylethylenediamine (3.73 g, 17.6 mmol) and triethylamine (5 ml) in 50 ml of dichloromethane a solution of 4,4'-Disulfanediyl-bis-benzenesulfonyl chloride (CB3.012) (3.32 g, 8.0 mmol) in dichloromethane (10 ml) was added slowly at 0° C. (ice-bath). The reaction mixture was stirred for 12 hours at room temperature and then concentrated under reduced pressure. The crude product was purified by chromatography on silica (first DCM, then DCM/methanol 25:1 as eluent). The product was obtained as a slightly yellow solid. Yield 5.65 g (7.37 mmol, 92%). m.p. 108–110° C.; $^1$H NMR (400 MHz, CDCl$_3$) d 4.16 (d, J=5.3 Hz, 2H), 4.44 (d, J=5.3 Hz, 2H), 7.07–7.14 (m, 20H), 7.20 (d, J=8.8 Hz, 4H), 7.35 (d, J=8.8 Hz, 4H); $^{13}$C NMR (100 MHz, CDCl$_3$) d 60.61 (+), 63.73 (+), 126.18 (+), 126.80 (+), 127.20 (+), 127.66 (+), 127.72 (+), 127.81 (+), 128.48 (+), 128.64 (+), 138.92 (C$_{quart}$), 139.29 (C$_{quart}$), 141.05 (C$_{quart}$), 141.12 (C$_{quart}$); MS (+FAB (3-NBA)) m/e 767 (47, M+1), 106 (100); [a]D$^{20}$ –87.0° (=1.31, EtOH).

(iv) Synthesis of Sodium (1S, 2S)-1,2-diphenylethylenediamine-N-phenylsulfonyl-4-sulfonate (CB3.016)

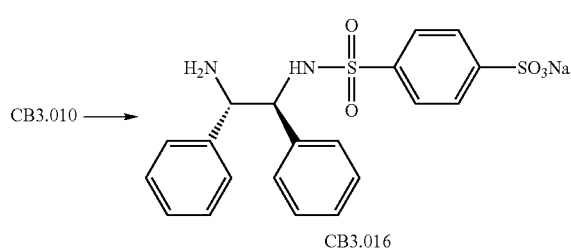

CB3.016: Sodium hydroxide solution (10 ml, 2.5M in water, 25 mmol) and hydrogen peroxide solution (5 ml, 27.5% by weight in water) were added a solution of CB3.010 (4.82 g, 6.28 mmol) in methanol (50 ml). An exothermic reaction resulted. The resulting mixture was stirred for 2 hours before another 2 ml or hydrogen peroxide solution were added. Stirring at room temperature was continued for 12 hours, then concentrated sodium hydrogen sulfite solution was added (10 ml) and the mixture was stirred for another 2 hours. The reaction mixture was concentrated to dryness under reduced pressure, water (50 ml) was added to dissolve the inorganic salts and the product was filtered off. The product was washed with cold water (100 ml) and dichloromethane (50 ml) and dried under high vacuum. Yield 4.454 g (10.3 mmol, 82%). m.p.>280° C. (dec.); $^1$H NMR (400 MHz, DMSO-d$_6$) d 4.43 (d, J=10.4 Hz, 1H), 4.65 (d, J=10.4 Hz, 1H), 6.79–6.93 (m, 5H), 7.19 (s, 5H), 7.41 (d, J=8.6 Hz, 2H), 7.45 (d, J=8.6 Hz, 2H), 8.61 (bs, 4); $^{13}$C NMR (100 MHz, DMSO-d$_6$) d 59.24 (+), 62.10 (+), 126.35 (+), 126.72 (+), 128.25 (+), 128.39 (+), 128.93 (+), 129.02 (+), 129.40 (+), 134.61 (C$_{quart}$), 136.14 (C$_{quart}$), 141.05 (C$_{quart}$), 152.03 (C$_{quart}$); MS (FAB(3-NBA)) m/e 433.1 (93, M+1), 165.0 (100); [a]$_D^{20}$ –76.9° (c=1.3, DMSO).

Example LS2

Preparation of Sodium (1R, 2R)-1,2-diaminocyclohexyl-N-phenylsulfonyl-4-sulfonate (CB3.019)

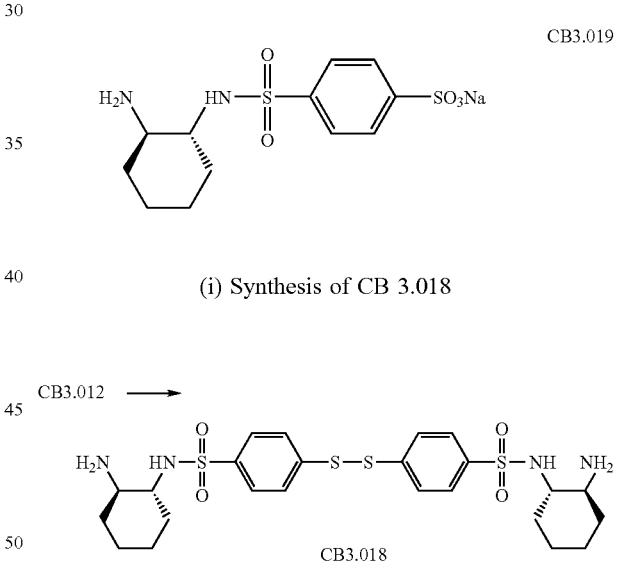

(i) Synthesis of CB 3.018

To solution of (R,R)-1,2-diaminocyclohexane (1.76 g, 15.4 mmol) and triethylamine (5 ml) in 50 ml of dichloromethane was added slowly a solution of 4,4'-Disulfanediyl-bis-benzenesulfonyl chloride (CB3.012) (2.91 g, 7.0 mmol) in dichloromethane (10 ml) at –78° C. (acetone/dry ice bath). The reaction mixture was allowed to warm up to room temperature stirred for 12 hours at this temperature and then concentrated under reduced pressure. The crude product was purified by chromatography on silica (first DCM, then DCM/methanol 5:1 as eluent). The product was obtained as a slightly yellow solid. Yield 3.44 g (6.02 mmol, 86%). m.p. 125–128° C.; $^1$H NMR (400 MHz, CD$_3$OD) d 1.01–1.34 (m, 10H), 1.53–1.65 (m, 4H), 1.86–1.98 (m, 2H), 2.35–2.45 (m, 2H), 2.74–2.82 (m, 2H, 7.69 (d, J=8.6 Hz, 4H), 7.84 (d, J=8.6 Hz, 4H); $^{13}$C NMR (100 MHz, CD$_3$OD)

d 25.49 (−), 26.13 (−), 33.05 (−), 33.79 (−), 55.77 (+), 60.31 (+), 127.84 (+), 128.70 (+), 141.94 ($C_{quart}$), 142.62 ($C_{quart}$); MS (FAB(3-NBA)) m/e 571 (100, M+1); $[a]D^{20}$ +36.5° (c=2.0, EtOH).

(ii) Synthesis of Sodium (1R, 2R)-1,2-diaminocyclohexyl-N-phenylsulfonyl-4-sulfonate (CB3.019)

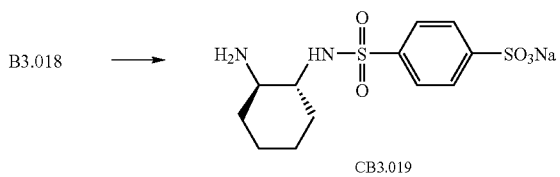

Sodium hydroxide solution (4 ml, 1M in water, 4 mmol) and hydrogen peroxide solution (2 ml, 27.5% by weight in water) were added to a solution of CB3.018 (1.142 g, 2.0 mmol) in methanol (20 ml). An exothermic reaction ensued. The resulting mixture was stirred for 2 hours before another 2 ml hydrogen peroxide solution were added. Stirring at room temperature was continued for 12 hours, then concentrated sodium hydrogen sulfite solution was added (5 ml) and the mixture was stirred for another 2 hours. The reaction mixture was concentrated to dryness under reduced pressure, water (20 ml) was added to dissolve the inorganic salts and the product was filtered off. The product was washed with cold water (40 ml), ethanol (20 ml), dichloromethane (50 ml) and dried under high vacuum. Yield 883 mg (2.64 mmol, 66%). m.p.>300° C.; $^1$H NMR (400 MHz, DMSO-$d_6$) d 0.90–1.38 (m, 7H), 1.84–1.98 (m, 1H), 2.66-2.82 (m, 1H), 2.88–3.02 (m, 1H), 7.82 (s, 4H), 7.89 (bs, 4H); $^{13}$C NMR (100 MHz, DMSO-$d_6$) d 23.80 (−), 24.69 (−), 29.95 (−), 31.21 (−), 54.22 (+), 55.62 (+), 126.90 (+), 127.17 (+), 142.00 ($C_{quart}$), 152.54 ($C_{quart}$), MS (−FAB(3-NBA)) m/e 333 (100, M−1); $[a]D_{20}$ +21.5° (c=1.7, DMSO).

Example LS3

Preparation of Sodium (1S, 2S)-1,2-diphenylethylenediamine-N-phenylsulfonyl-2-sulfonate (3.022)

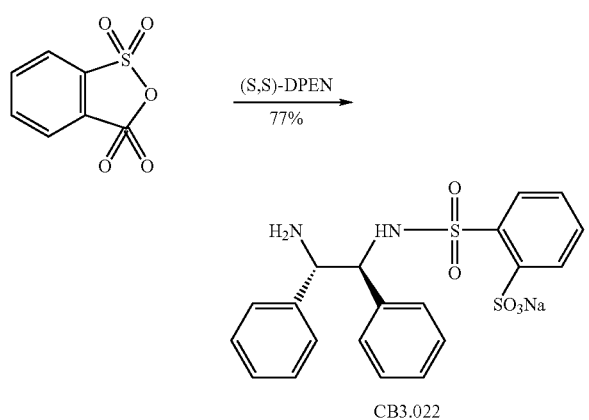

Benzene-1,2-disulfonic acid anhydride (1.30 g, 5.9 mmol) was added to a solution of (S,S)-diphenylethylenediamine (1.25 g, 5.9 mmol) in 150 ml of dichloromethane at room temperature. The reaction mixture was stirred for 1 hour and then concentrated under reduced pressure. Isopropanol (50 ml) was added to the residue and the mixture heated to reflux for 15 minutes. After cooling to room temperature the product precipitated and was collected in a sinter-funnel and washed with isopropanol (50 ml). The product is dried under high vacuum at 60° C. for 12 hours. Yield 1.96 g (4.54 mmol, 77%). m.p.>250° C.; $^1$H NMR (400 MHz, d6-DMSO) d 4.60 (d, J=11.9 Hz, 1H), 4.69 (dd, J=11.9, 8.2 Hz, 1H), 6.71–6.79 (m, 5H), 7.12 (dt, J=7.8, 1.2 Hz, 1H), 7.16–7.19 (m, 5H), 7.35 (dt, J=7.8, 1.2 Hz, 1H), 7.43 (dd, J=7.8, 1.2 Hz, 1H), 7.43 (dd, J=7.8, 1.2 Hz, 1H), 7.83 (dd, J=7.8, 1.2 Hz, 1H), 8.66 (s, 3H), 8.88 (d, J=8.2 Hz, 1H); $^{13}$C NMR (100 MHz, d6-DMSO) d 60.61 (30 ), 63.73 (+), 126.18 (+), 126.80 (+), 127.20 (+), 127.66 (+), 127.72 (+), 127.81 (+), 128.48 (+), 128.64 (+), 138.92 ($C_{quart}$), 139.29 ($C_{quart}$), 141.05 ($C_{quart}$), 141.12 ($C_{quart}$); MS (+FAB(3-NBA)) m/e 767 (47, M+1), 106 (100); $[a]D^{20}$ −87.0° (c=1.31, EtOH).

Example LS4

Synthesis of Sodium (1R, 2R)-1,2-diphenylethylenediamine-N-phenylsulfonyl-4-sulfonate (TT-CB4)

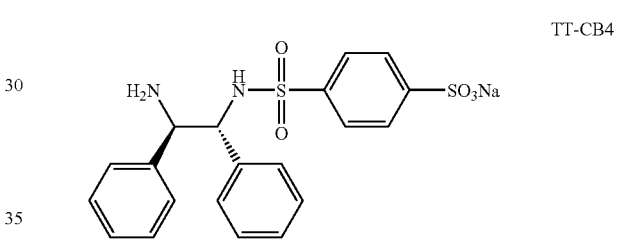

The preparation of TT-CB4 was undertaken in an identical manner to CB3.016 (Example LS1) but using R,R-diphenylethylenediamine in place of S,S-diphenylethylenediamine.

Catalyst Preparation and Hydrogenation Section.

Unless otherwise stated, the following procedures were employed for each of Examples TH5–TH19 below.

(a) Catalyst Preparation

In a Schlenk flask (25 ml) with a magnetic stirring-bar a solution of KOt-Bu in isopropanol (0.8 ml of a 0.1 M solution, 0.08 mmol) was added to a suspension of ligand (0.08 mmol) in water (1 ml) and stirred under $N_2$-atmosphere at room temperature until a clear solution was obtained. To this solution the transition metal compound (0.01 mmol) was added and the mixture stirred under an argon atmosphere at 40° C. for two hours.

(b) Hydrogenation

After cooling of the solution obtained in (i) to 22° C. the substrate to be hydrogenated (2 mmol) in isopropanol (10 ml) and KOt-Bu in isopropanol (2.0 ml of a 0.1 M solution, 0.20 mmol) were added to start the reaction.

Samples were taken out of the reaction mixture at various times and analysed by gas chromatography (β-dex column).

The ligand, transition metal compound and hydrogenation substrate used are tabulated below for each Example together with the results obtained in the hydrogenation reaction.

Example TH5

This Example demonstrates ruthenium catalysed asymmetric transfer hydrogenation of acetophenone in accordance with the equation:

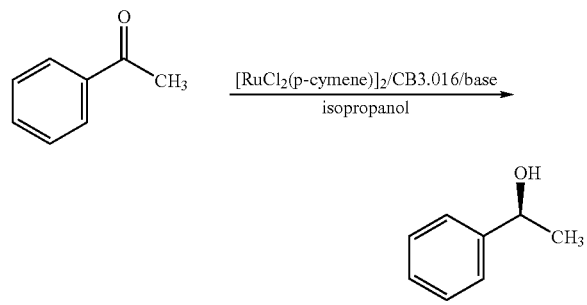

The reagents used were as follows

| Transition Metal Compound | [RuCl$_2$(p-cymene)]$_2$ | 6.1 mg |
|---|---|---|
| Ligand | CB3.016 | 34.6 mg |
| Hydrogenation Substrate | Acetophenone | 240 mg |

The results are shown in Table 1.

TABLE 1

Ruthenium/CB3.016/acetophenone. Hydrogenation at 22° C.

| Time [h] | T [° C.] | Conversion [%] | ee [%] |
|---|---|---|---|
| 3 | 22 | 16 | 95.0 |
| 20 | 22 | 61 | 95.3 |
| 28 | 22 | 74 | 95.3 |
| 44 | 22 | 96 | 94.4 |

Example TH6

Example TH5 was repeated save that in step (a) stirring was effected at 22° C. (rather than 40° C.) and that step (b) was carried out at temperatures of 22° C., 30° C. and 40° C.

The results are shown in Tables 2 to 4.

TABLE 2

Ruthenium/CB3.016/Acetophenone Hydrogenation at 22° C.

| Time [h] | T [° C.] | Conversion [%] | ee [%] |
|---|---|---|---|
| 1 | 22 | 3 | — |
| 2 | 22 | 7 | — |
| 3 | 22 | 10 | — |
| 4 | 22 | 13 | — |
| 16 | 22 | 39 | 96.3 |
| 25 | 22 | 51 | 95.3 |
| 41 | 22 | 58 | 96.3 |
| 69.5 | 22 | 62 | 96.0 |

TABLE 3

Ruthenium/CB3.016/Acetophenone at 30° C.

| Time [h] | T [° C.] | Conversion [%] | ee [%] |
|---|---|---|---|
| 1 | 30 | 10 | 95.0 |
| 2 | 30 | 19 | — |
| 3 | 30 | 26 | — |
| 4 | 30 | 34 | 95.7 |
| 16 | 30 | 68 | 95.2 |
| 25 | 30 | 73 | 95.5 |
| 41 | 30 | 77 | 95.1 |
| 69.5 | 30 | 77 | 94.2 |

TABLE 4

Ruthenium/CB3.016/Acetophenone at 40° C.

| Time [h] | T [° C.] | Conversion [%] | ee [%] |
|---|---|---|---|
| 1 | 40 | 31 | 95.2 |
| 2 | 40 | 48 | 94.4 |
| 3 | 40 | 58 | 95.6 |
| 4 | 40 | 66 | 94.6 |
| 16 | 40 | 89 | 94.2 |
| 25 | 40 | 90 | 93.7 |
| 41 | 40 | 92 | 93.5 |
| 69.5 | 40 | 91 | 93.4 |

The temperature-effect is significant, but in all cases a slowdown or standstill of the reaction after about 20 h was observed, probably due to precipitation of the catalyst.

The drop in enantioselectivity was not as high as expected.

Example TH7

This Example demonstrates the rhodium catalysed transfer hydrogenation of acetophenone using CB3.016 as a ligand for the catalyst.

The following reactants were employed.

| Transition Metal Compound | [1]Rh(Cp*)Cl$_2$]$_2$ |
|---|---|
| Ligand | CB3.016 |
| Hydrogenation Substrate | Acetophenone |

[1][Rh(pentamethylcyclodienyl)Cl$_2$]$_2$

The results obtained are shown in Table 5.

TABLE 5

Rhodium/CB3.016/Acetophenone

| Time [h] | T [° C.] | Conversion [%] | ee [%] |
|---|---|---|---|
| 1 | 22 | 34 | 97 |
| 18 | 22 | 72 | 97 |

Example TH8

This Example demonstrates the ruthenium catalysed transfer hydrogenation of acetophenone using CB3.019 as catalyst ligand.

The following reactants were used.

| Transition Metal Compound | [RuCl$_2$(p-cymene)]$_2$ |
|---|---|
| Ligand | CB3.019 |
| Hydrogenation Substrate | Acetophenone |

The results are shown in Table 6

TABLE 6

Ruthenium/CB3.019/Acetophenone

| Time [h] | Conversion [%] | ee [%] |
|---|---|---|
| 1 | 1 | — |
| 19.5 | 28 | 88.0 |
| 28 | 40 | 90.7 |
| 51 | 54 | 90.8 |
| 96 | 67 | 89.8 |

Example TH9

This Example demonstrates the rhodium catalysed transfer hydrogenation of acetophenone using CB3.019 as catalyst ligand.

The following reactants were used.

| Transition Metal Compound | [Rh(Cp*)Cl$_2$]$_2$ |
|---|---|
| Ligand | CB3.019 |
| Hydrogenation Substrate | Acetophenone |

The results are shown in Table 7

TABLE 7

Rhodium/CB3.019/Acetophenone.

| Time [h] | Conversion [%] | ee [%] |
|---|---|---|
| 1 | 62 | 97.6 |
| 19.5 | 94 | 94.9 |
| 28 | 94 | 94.5 |
| 51 | 94 | 94.6 |
| 96 | 96 | 94.5 |

Comparing the results of Examples TH8 and TH9, the rhodium-catalysed system proved to be more reactive and selective compared to the ruthenium one. The enantioselectivity was close to 98% after 1 h and dropped slightly at the end to 94.5%.

Example TH10

This Example investigates the use of a catalysts based on ruthenium and either CB3.016, CB3.019 or CB.022 in the hydrogenation of a range of aromatic ketones as hydrogenation substrate. The hydrogenation procedure used was as described previously save that 1 cm$^3$ of water was added additionally to the isopropanol and KOt-By. The water concentration was thus 15%.

The following reactants were used

| Transition Metal Compound | [RuCl$_2$(p-cymene)]$_2$ |
|---|---|
| Ligand (1) | CB3.016 |
| Ligand (2) | CB-3.019 |
| Ligand (3) | CB3.022 |
| Hydrogenation Substrate | (5)–(10) See below |

5

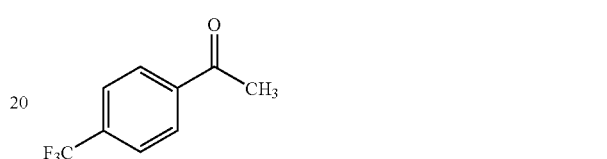

6

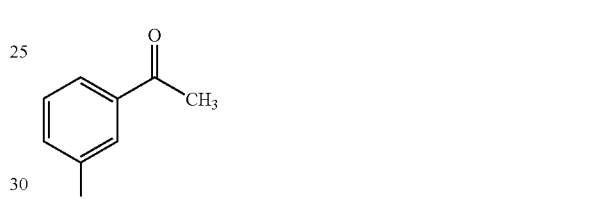

7

8

9

10

The results are shown in Table 8.

TABLE 8

Ruthenium/CB3.016(1) or CB3.019(2) or CB3.022(3)/Ketones(5)–(10).

| Ketone | Ligand | Reaction time [h] | Conversion [%] | Ee [%] |
|---|---|---|---|---|
| 5 | 1 | 48 | 96 | 94 |
| 5 | 2 | 48 | 91 | 88 |
| 5 | 3 | 48 | 11 | 91 |
| 6 | 1 | 4 | 100 | 81 |

TABLE 8-continued

Ruthenium/CB3.016(1) or CB3.019(2) or CB3.022(3)/Ketones(5)–(10).

| Ketone | Ligand | Reaction time [h] | Conversion [%] | Ee [%] |
|---|---|---|---|---|
| 6 | 2 | 4 | 100 | 88 |
| 7 | 1 | 24 | 90 | 87 |
| 7 | 2 | 24 | 91 | 81 |
| 8 | 1 | 18 | 10 | 24 |
| 8 | 2 | 18 | 18 | 55 |
| 9 | 1 | 42 | 31 | 91 |
| 9 | 2 | 42 | 35 | 83 |
| 10 | 1 | 72 | 94 | 95 |
| 10 | 2 | 48 | 87 | 90 |

Example TH11

Example TH10 was repeated but using [Rh(Cp*)Cl$_2$]$_2$ as the transition metal compound. Thus, the reactants were as follows:

| | |
|---|---|
| Transition Metal Compound | [Rh(Cp*)Cl$_2$]$_2$ |
| Ligand (1) | TT-CB4 |
| Ligand (2) | CB3.019 |
| Hydrogenation Substrate | (5)–(10) See above |

The results are shown in Table 9.

TABLE 9

Rhodium/TT-CB4(1) or CB3.019(2)/Ketones(5)–(10)

| Ketone | Ligand | Reaction time [h] | Conversion [%] | ee [%] |
|---|---|---|---|---|
| 5 | 1 | 24 | 92 | 97 |
| 5 | 2 | 18 | 94 | 95 |
| 6 | 1 | 4 | 100 | 83 |
| 6 | 2 | 2 | 100 | 88 |
| 7 | 1 | 18 | 98 | 95 |
| 7 | 2 | 4 | 99 | 94 |
| 8 | 1 | 18 | 2 | 22 |
| 8 | 2 | 18 | 40 | 76 |
| 9 | 1 | 42 | 9 | 94 |
| 9 | 2 | 42 | 65 | 95 |
| 10 | 1 | 64 | 81 | 82 |
| 10 | 2 | 48 | 95 | 96 |

The results in tables 8 and 9 show the effectiveness of TT-CB4 and CB3.019 in transfer hydrogenations. p-Trifluoromethyl acetophenone (6) reacts rapidly and quantitatively giving moderate and very similar ee's in the ruthenium and rhodium catalysed reaction. m-Trifluoromethyl acetophenone (7) reacts slightly more slowly giving a very high ee only in the rhodium catalysed reaction. o-Trifluoromethyl acetophenone (8) reacts very slowly, compared to (6) and (7). Only the rhodium-catalysed reaction using ligand (2) shows moderate enantioselectivity. The electron-rich p-methoxy acetophenone (9) reacts relatively slowly, as expected. It was not possible to obtain a conversion above 65% under these conditions. 2-Acetylnaphthalene (10) reacts similarly to acetophenone.

Example TH12

The Example demonstrates the ruthenium catalysed transfer hydrogenation of acetophenone using TT-CB4 as catalyst ligand.

| | |
|---|---|
| Transition Metal Compound | [RuCl$_2$(p-cymene)]$_2$ |
| Ligand | TT-CB4 |
| Hydrogeneration Substrate | Acetophenone |

The results are shown in Table 10.

TABLE 10

Ruthenium/TT-CB4/Acetophenone

| Reaction Time (hours) | Conversion *(%) | Enantiomeric excess (%) |
|---|---|---|
| 19 | 30 | 94.4 |
| 24.5 | 34 | 95.0 |
| 42.5 | 46 | 94.4 |
| 49 | 48 | 94.2 |
| 66 | 55 | 94.4 |
| 73 | 58 | 94.3 |
| 90 | 62 | 94.4 |
| 96 | 64 | 94.4 |

Example TH13

Example TH12 was repeated using 4-Bromoacetophenone as hydrogenation substrate in place of acetophenone. The following reactants were employed.

| | |
|---|---|
| Transition Metal Compound | [RuCl$_2$(p-cymene)]$_2$ |
| Ligand | TT-CB4 |
| Hydrogenation Substrate | 4-Bromoacetophenone |

The results shown in Table 11

TABLE 11

Ruthenium/TT-CB4/4-Bromoacetophenone

| Reaction Time (hours) | Conversion (%) | Enantiomeric excess (%) |
|---|---|---|
| 20.5 | 43 | 92.4 |
| 27 | 51 | 92.4 |
| 44 | 67 | 92.3 |
| 50.5 | 73 | 92.4 |
| 67.5 | 82 | 92.3 |
| 73.5 | 85 | 92.3 |
| 139 | 98 | 92.1 |

Example TH14

Example TH13 was repeated but using 2-Fluoroacetophenone as hydrogenation substrate.

The following reactants were employed.

| | |
|---|---|
| Transition Metal Compound | [RuCl$_2$(p-cymene)]$_2$ |
| Ligand | TT-CB4 |
| Hydrogenation Substrate | 2-Fluoroacetophenone |

The results are shown in Table 12.

TABLE 12

Ruthenium/TT-CB4/2-Fluooacetophenone

| Reaction Time (hours) | Conversion (%) | Enantiomeric excess (%) |
|---|---|---|
| 2 | 7 | 73.3 |
| 19 | 41 | 75.1 |
| 26 | 48 | 75.1 |
| 43 | 64 | 75.0 |
| 48.5 | 69 | 75.3 |
| 114.5 | 91 | 75.2 |

Comparing the results of Examples TH12 to TH14, it can be seen that the rates of these reactions are generally quite low. However, the presence of an electron-withdrawing group 2-fluoroacetophenone increases the rate of reaction. The enantioselectivities are high except in the case of the reduction of 2-fluoroacetophenone. This result is not surprising given that the fluoro substituent is in the ortho position. It can also be seen that the enantiomeric excess does not decrease over time as would be expected.

Example TH15

This Example describes the iridium catalysed hydrogenation of acetophenone using TT-CB4 as catalyst ligand. The hydrogenation procedure used was the same as that of Example TH10 (15% water)

The following reactants were employed.

| Transition Metal Compound | [1][Ir(Cp)Cl$_2$]$_2$ |
|---|---|
| Ligand | TT-CB4 |
| Hydrogenation Substrate | (a)–(k) See below |

[1] [Ir(pentamethylcyclopentadienyl)$_2$Cl$_2$]$_2$

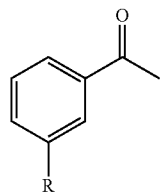

a: R=H
b: R=F
h: R=CF$_3$

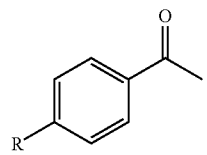

c: R=Cl
d: R=Br
i: R=OMe

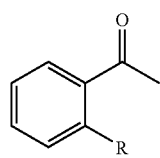

e: R=F f: R=Br
g: R=Cl

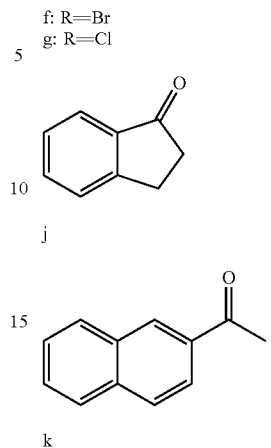

j k

The results are shown in Table 13.

TABLE 13

Iridium/TT-CB4/ketones (a)–(k)

| Ketone | Reaction Time (h) | Conversion (%) | Ee (%) |
|---|---|---|---|
| a | 140 | 90 | 82 |
| b | 51 | 83 | 85 |
| c | 91 | 89 | 76 |
| d | 91 | 93 | 76 |
| e | 68 | 86 | 36 |
| F | 163 | 65 | 29 |
| G | 163 | 89 | 24 |
| H | 43 | 95 | 86 |
| I | 150 | 22 | 78 |
| J | 139 | 41 | 91 |
| K | 139 | 77 | 73 |

Example TH16

Example TH15 was repeated but using CB-3.019 as ligand in place of TT-CB4.

The following reactants were employed.

| Transition Metal Compound | [Ir(Cp*)Cl$_2$]$_2$ |
|---|---|
| Ligand | CB-3.019 |
| Hydrogenation Substrate | Ketones (a)–(k) |

The results are shown in Table 14

TABLE 14

Iridium/CB-3.019/ketones (a)–(k).

| Ketone | Reaction Time (h) | Conversion (5) | ee(%) |
|---|---|---|---|
| a | 26 | 88 | 96 |
| b | 26 | 99 | 94 |
| c | 25 | 98 | 94 |
| d | 20 | 99 | 95 |
| e | 21 | 99 | 73 |
| f | 92 | 95 | 66 |
| g | 46 | 96 | 63 |
| h | 4 | 98 | 93 |
| i | 141 | 80 | 95 |
| j | 45 | 55 | 97 |
| k | 45 | 96 | 96 |

There are noticeable differences in the results obtained for ruthenium and iridium with ligand 1 (TT-CB4). Generally, the ruthenium system gives rise to higher enantiomeric excess and lower reaction rate, whereas the iridium system gives a higher reaction rate and a lower enantiomeric excess. However, the combination of iridium and ligand 2 proved to be most successful. The reactions tended to proceed rapidly with high enantioselectivity. For all systems, electron deficient ketones were reduced more quickly. This is best illustrated by comparing the results of the reduction of 3-trifluoromethylacetophenone and 4-methoxyacetophenone. Also, as expected, substrates with ortho-groups gave rise to a lower reactivity and enantiomeric excess.

Example TH17

In order to determine the effect of an increase in water concentration, the procedures of Examples TH14 and 15 were repeated but using a 2-propanol-water mixture containing (i) 34% and (ii) 51% water. The overall volume of reaction solvent remained unchanged.

The following reactants were employed.

| Transition Metal Compound | [Ir(Cp*)Cl$_2$]$_2$ |
|---|---|
| Ligand (1) | TT-CB4 |
| Ligand (2) | CB-3.019 |
| Hydrogenation Substrate | Ketones (a)–(k) |

The results are shown in Table 15.

TABLE 15

| Iridium/TT-CB4(1) or CB3.019(2)/Ketones (a)–(k) | | | |
|---|---|---|---|
| Ketone | Ligand | Reaction Time(h) | Conversion (%) | ee(%) |
| b$^i$ | 1 | 22 | 74 | 92 |
| b$^{ii}$ | 1 | 22 | 90 | 92 |
| b$^i$ | 2 | 2.5 | 82 | 94 |
| b$^{ii}$ | 2 | 2.5 | 94 | 93 |
| e$^{ii}$ | 2 | 5 | 97 | 74 |
| i$^i$ | 1 | 115 | 20 | 84 |
| i$^{ii}$ | 1 | 115 | 33 | 91 |
| i$^i$ | 2 | 116 | 76 | 92 |
| i$^{ii}$ | 2 | 116 | 89 | 87 |
| k$^i$ | 1 | 42 | 47 | 91 |
| k$^{ii}$ | 1 | 42 | 66 | 93 |
| k$^i$ | 2 | 18 | 92 | 95 |
| k$^{ii}$ | 2 | 18 | 92 | 94 |

Table 3. Iridium systems containing (i) 34% and (ii) 51% water.

The results shown in Table 15 are surprising in that in expected rate decrease relating to the lower concentration of 2-propanol was not observed. Instead, a significant rate increase was noted for both the (i) 34% and (ii) 51% water systems. In addition to this, iridium-ligand 1 systems showed a large increase in enantiomeric excess when the concentration of water was increased form 15% to 34% (see F results shown in Table 13.).

Example LS18

This Example demonstrates the synthesis of a further ligand:

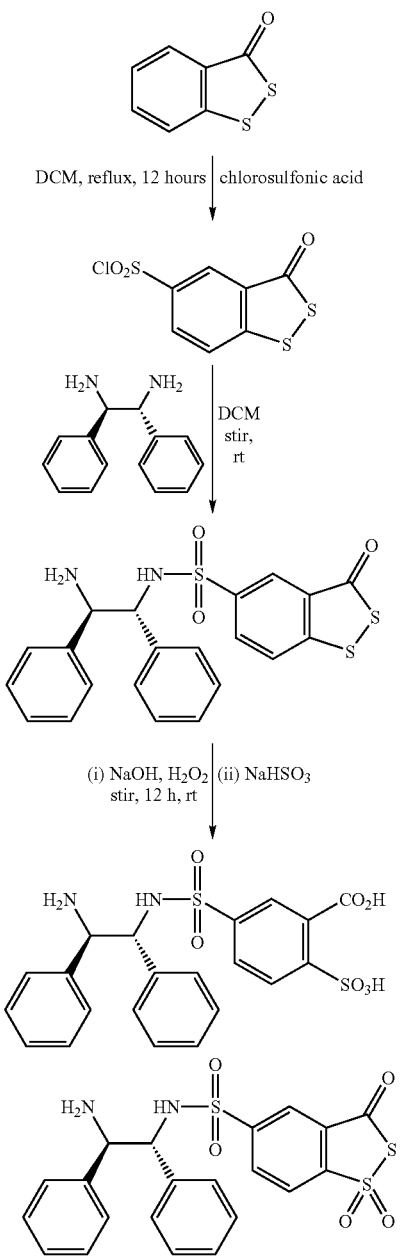

Example TH19

Bis-3,5-trifluoromethylacetophenone (1.32 g, 5.16 mmoles), dichloro(pentamethylcyclopentadienyl)rhodium (III) dimmer (7.4 mg, 11.97 micromoles), sodium (1S,2S) 4-(2-Amino-1,2-diphenyl-ethylsulfamoyl)-benzenesulfonate (11.2 mg, 25.92 micromoles), and 2.5 ml tetrahydrofuran were charged to a 25 ml flask and flushed with nitrogen. Water (12 microlitres, 0.66 mmoles) was added by syringe and the mixture was stirred for 20 minutes. A 2:5 molar ratio mixture of triethylamine and formic acid were added to the reaction at a rate of 1.5 ml/h for 2 h. At this time all the ketone had been converted to alcohol and the optical purity was determined to be 81% ee. The reaction was concentrated by vacuum distillation a sample A was taken for Rhodium analysis. To the concentrate, 3 ml toluene and 5 ml water was added, the aqueous phase separated and the organic layer divided into three portions B, C, D of 1 ml. To each portion was added 1.6 ml water. Sample B was concentrated to dryness. To sample C 100 mg of Amberlite™ IRA-93 was added and the mixture stirred for 2 hours, filtered and the filtrate concentrated to dryness. To sample D 100 mg of Dowex™ 1×8–50 was added and the mixture stirred for 2 hours, filtered and the filtrate concentrated to dryness. In sample B the concentrated filtrate was dark purple, whilst in samples C and D it was a light pink.

The samples were analysed by ICPMS for Rhodium and the following results were obtained:

| | |
|---|---|
| Sample A | 4930 ppm |
| Sample B | 1040 ppm |
| Sample C | 365 ppm |
| Sample D | 280 ppm |

The results from the analysis of Samples C and D compared to Sample B show that treatment of the reaction mixture with ion exchange resins is effective in the separation of the catalyst from the reaction mixture.

The invention claimed is:

1. A catalyst having the general formula:

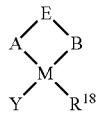

in which:
$R^{18}$ represents an optionally substituted hydrocarbyl or perhalogenated hydrocarbyl ligand;

A represents $-NR^{19}-$, $-NR^{20}-$, $-NHR^{19}$, $-NR^{19}R^{20}$ or $-NR^{20}R^{21}$ where $R^{19}$ is H, $C(O)R^{21}$, $SO_2R^{21}$, $C(O)NR^{21}R^{25}$, $C(S)NR^{21}R^{25}$, $C(=NR^{25})SR^{28}$ or $C(=NR^{25})OR^{26}$, $R^{20}$ and $R^{21}$ each independently represents an optionally substituted hydrocarbyl, perhalogenated hydrocarbyl or an optionally substituted heterocyclyl group, and $R^{25}$ and $R^{26}$ are each independently hydrogen or a group as defined for $R^{21}$;

B represents $-O-$, $-OH$, $OR^{22}$, $-S-$, $-SH$, $SR^{22}$, $-NR^{22}-$, $-NR^{23}-$, $-NHR^{23}$, $-NR^{22}R^{23}$, $-NR^{22}R^{24}$, $-PR^{22}-$ or $PR^{22}R^{24}$ where $R^{23}$ is H, $C(O)R^{24}$, $SO_2R^{24}$, $C(O)NR^{24}R^{27}$, $C(S)NR^{24}R^{27}$, $C(=NR^{27})SR^{28}$ or $C(=NR^{27})OR^{28}$, $R^{22}$ and $R^{24}$ each independently represents an optionally substituted hydrocarbyl, perhalogenated hydrocarbyl or an optionally substituted heterocyclyl group, and $R^{27}$ and $R^{28}$ are each independently hydrogen or a group as defined for $R^{24}$;

E represents a linking group comprising 2–4 carbon atoms linking A and B, said carbon atoms optionally carrying one or more substituents;

M represents a Group VIII transition metal capable of catalysing transfer hydrogenation; and Y represents an anionic group, a basic ligand or a vacant site;

provided that when Y is not a vacant site that at least one of A or B carries a hydrogen atom, characterised in that at least one of said groups $R^{20}$ to $R^{22}$ or $R^{24}$ to $R^{28}$ is present in the form of an optionally substituted sulphonated hydrocarbyl group, a sulphonated perhalogenated hydrocarbyl group, or an optionally substituted sulphonated heterocyclyl group.

2. A catalyst according to claim 1 wherein A represents $-NR^{19}-$, $-NR^{20}-$, $-NHR^{19}$, $-NR^{19}R^{20}$ or $-NR^{20}R^{21}$ where $R^{19}$ is H, $C(O)R^{21}$, $SO_2R^{21}$, $C(O)NR^{21}R^{25}$, $C(S)NR^{21}R^{25}$, $C(=NR^{25})SR^{26}$ or $C(=NR^{25})OR^{26}$, $R^{20}$ and $R^{21}$ each independently represents an optionally substituted hydrocarbyl, perhalogenated hydrocarbyl or an optionally substituted heterocyclyl group, and $R^{25}$ and $R^{26}$ are each independently hydrogen or a group as defined for $R^{21}$;

B represents $-O-$, $-OH$, $OR^{22}$, $-NR^{22}-$, $-NR^{23}-$, $-NHR^{23}$, $-NR^{22}R^{23}$, or $-NR^{22}R^{24}$ where $R^{23}$ is H, $C(O)R^{24}$, $SO_2R^{24}$, $C(O)NR^{24}R^{27}$, $C(S)NR^{24}R^{27}$, $C(=NR^{27})SR^{28}$ or $C(=NR^{27})OR^{28}$, $R^{22}$ and $R^{24}$ each independently represents an optionally substituted hydrocarbyl, perhalogenated hydrocarbyl or an optionally substituted heterocyclyl group, and $R^{27}$ and $R^{28}$ are each independently hydrogen or a group as defined for $R^{24}$; and wherein at least one of $R^{20}$ to $R^{22}$ or $R^{24}$ to $R^{28}$ is present in the form of an optionally substituted sulphonated hydrocarbyl group, a sulphonated perhalogenated hydrocarbyl group or an optionally substituted sulphonated heterocyclyl group.

3. A catalyst according to claim 2 wherein A is a group of the formula $-NHR^{19}$ or $-NR^{19}-$ where $R^{19}$ is represented by the group $-SO_2R^{21}$ in which $R^{21}$ is an optionally substituted sulphonated hydrocarbyl group, sulphonated perhalogenated hydrocarbyl group or optionally substituted sulphonated heterocyclyl group.

4. A catalyst according to claim 3 wherein $R^{21}$ is a sulphonated phenyl group having n sulphonate groups where n is 1 to 5.

5. A catalyst according to claim 3 or 4 wherein B is $-NH_2$ or $-NH-$.

6. A catalyst according to claim 1 wherein E is of the formula $-CHR^{30}-CHR^{31}-$ where $R^{30}$ and $R^{31}$ are independently hydrogen or an optionally substituted hydrocarbyl group.

7. A catalyst according to claim 1 wherein E has two carbon atoms linking A and B and is a bond in an optionally substituted cycloaliphatic ring.

8. A catalyst according to claim 1 or 4 wherein $R^{18}$ is an optionally substituted aryl or an optionally substituted alkene.

9. A catalyst according to claim 8 wherein $R^{18}$ is cymene.

10. A catalyst according to claim 8 wherein $R^{18}$ is a pentamethylcyclopentadienyl group.

11. A catalyst according to claim 1, wherein M is ruthenium, rhodium or iridium.

12. A catalyst according to claim 1 or 4, in which A—E—B comprises at least one stereospecific centre.

13. A process for the preparation of a catalyst according to claim 1 or 4 which comprises reacting a metal aryl halide complex or a metal alkenyl halide complex with a compound of formula A—E—B or a protonated equivalent from which it may be derived.

14. A ligand having the following formula:

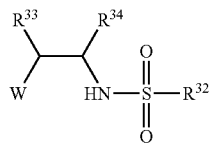

in which:

W represents —OH or —NH$_2$;

R$^{32}$ represents an aryl group having at least one —SO$_3$H or —S$_3$M$^1$ substituent wherein M$^1$ is an alkali metal and is further optionally substituted; and R$^{33}$, R$^{34}$ are independentiy optionally substituted hydrocarbyl groups or R$^{33}$ and R$^{34}$ are optionally linked in such a way as to define an optionally substituted ring.

15. A ligand according to claim 14 in which R$^{32}$ is a phenyl group having one —SO$_3$H or —S$_3$M$^1$ substituent.

16. A ligand according to claim 14 or 15 in which R$^{33}$ and are independently phenyl.

17. A ligand according to claim 14 or 15 in which R$^{33}$ and R$^{34}$ are linked so as to define a cyclohexyl ring.

18. The compound:

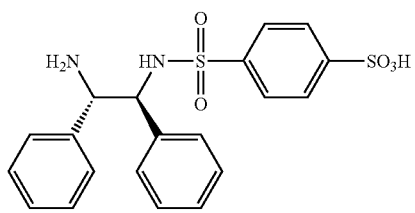

and salts thereof.

19. The compound:

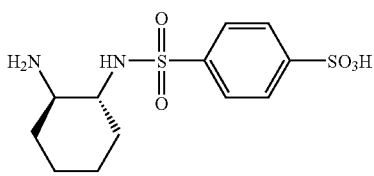

and salts thereof.

20. The compound:

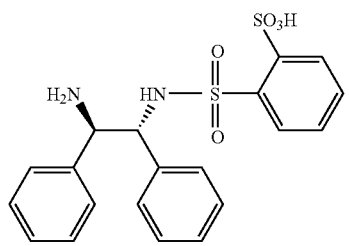

and salts thereof.

21. The compound:

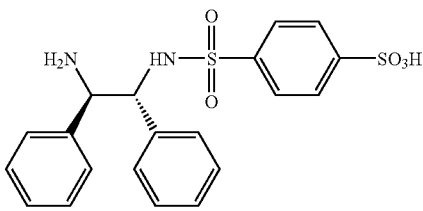

and salts thoroof.

22. A process comprising reacting a di-sulphide of formula:

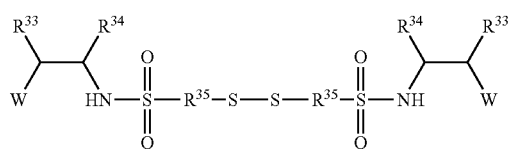

with an oxidant to produce a compound of formula:

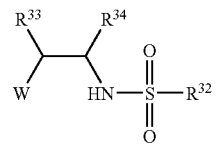

wherein:

W is —OH or —N H$^2$;

R$^{32}$ is an aryl group having at least one —SO$_3$H or SO$_3$M$^1$ (M$^1$ =alkali metal) substituent;

R$^{35}$ is an aryl group; and

R$^{33}$, R$^{34}$ are independently optionally substituted hydrocarbyl groups or R$^{33}$ and R$^{34}$ are optionally linked in such a way as to define an optionally substituted ring.

23. A process according to claim 22 wherein the substitution pattern of the aryl group R$^{32}$ is such that the —SO$_3$H or SO$_3$M$^1$ (M$^1$=alkali metal) substituent is positioned para with respect to the SO$_2$NH—CHR$^{34}$—CHR$^{33}$—W group.

24. A process according to claim 22 or 23 wherein the oxidant is alkaline hydrogen peroxide.

25. A process for the transfer hydrogenation of an organic compound having a carbon-carbon or carbon-heteroatom double bond, said process comprising reacting the organic compound with a hydrogen donor in the presence of a catalyst having the general formula:

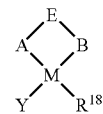

in which:

R$^{18}$ represents an optionally substituted hydrocarbyl or perhalogenated hydrocarbyl ligand;

A represents —NR$^{19}$—, —NR$^{20}$, —NHR$^{19}$, —NR$^{19}$R$^{20}$ or —NR$^{20}$R$^{21}$ where R$^{19}$ is H, C(O)R$^{21}$, SO$_2$R$^{21}$, $C(O)NR^{21}R^{25}$, $C(S)NR^{21}R^{25}$, $C(=NR^{25})SR^{26}$ or $C(=NR^{25})OR^{26}$, $R^{20}$ and $R^{21}$ each independently represents an optionally substituted hydrocarbyl, perhalogenated hydrocarbyl or an optionally substituted heterocyclyl group, and $R^{25}$ and $R^{26}$ are each independently hydrogen or a group as defined for $R^{21}$;

B represents —O—, —OH, $OR^{22}$, —S—, —SH, $SR^{22}$, —$NR^{22}$—, —$NR^{23}$—, —$NHR^{23}$, —$NR^{22}R^{23}$, —$NR^{22}R^{24}$, —$PR^{22}$— or —$PR^{22}R^{24}$ where $R^{23}$ is H, $C(O)R^{24}$, $SO_2R^{24}$, $C(O)NR^{24}R^{27}$, $C(S)NR^{24}R^{27}$, $C(=NR^{27})SR^{28}$ or $C(=NR^{27})OR^{28}$, $R^{22}$ and $R^{24}$ each independently represents an optionally substituted hydrocarbyl, perhalogenated hydrocarbyl or an optionally substituted heterocyclyl group, and $R^{27}$ and $R^{28}$ are each independently hydrogen or a group as defined for $R^{24}$;

E represents a linking group;

M represents a metal capable of catalysing transfer hydrogenation; and

Y represents an anionic group, a basic ligand or a vacant site;

provided that when Y is not a vacant site that at least one of A or B carries a hydrogen atom, characterised in that at least one of said groups $R^{20}$ to $R^{22}$ or $R^{24}$ to $R^{28}$ is present in the form of an optionally substituted suiphonated hydrocarbyl group, a sulphonated perhalogenated hydrocarbyl group, or an optionally substituted sulphonated heterocyclyl group.

26. A process according to claim 25 wherein A represents —$NR^{19}$—, —$NR^{20}$—, —$NHR^{19}$, —$NR^{19}R^{20}$ or —$NR^{20}R^{21}$ where $R^{19}$ is H, $C(O)R^{21}$, $SO_2R^{21}$, $C(O)NR^{21}R^{25}$, $C(S)NR^{21}R^{25}$, $C(=NR^{25})SR^{26}$ or $C(=NR^{25})OR^{26}$, $R^{20}$ and $R^{21}$ each independently represents an optionally substituted hydrocarbyl, perhalogenated hydrocarbyl or an optionally substituted heterocyclyl group, and $R^{25}$ and $R^{26}$ are each independently hydrogen or a group as defined for $R^{21}$;

B represents —O—, —OH, $OR^{22}$, —$NR^{22}$—, —$NR^{23}$—, —$NHR^{23}$, —$NR^{22}R^{23}$, or —$NR^{22}R^{24}$ where $R^{23}$ is H, $C(O)R^{24}$, $SO_2R^{24}$, $C(O)NR^{24}R^{27}$, $C(S)NR^{24}R^{27}$, $C(=NR^{27})SR^{28}$ or $C(=NR^{27})OR^{28}$, $R^{22}$ and $R^{24}$ each independently represents an optionally substituted hydrocarbyl, perhalogenated hydrocarbyl or an optionally substituted heterocyclyl group, and $R^{27}$ and $R^{28}$ are each independently hydrogen or a group as defined for $R^{24}$; and wherein at least one of $R^{20}$ to $R^{22}$ or $R^{24}$ to $R^{28}$ in the form of an optionally substituted sulphonated hydrocarbyl group, a sulphonated perhalogenated hydrocarbyl group or an optionally substituted sulphonated heterocyclyl group.

27. A process according to claim 26 wherein A is a group of the formula —$NHR^{19}$ or —$NR^{19}$— where $R^{19}$ is represented by the group —$SO_2R^{21}$ in which $R^{21}$ is an optionally substituted sulphonated hydrocarbyl group, sulphonated perhalogenated hydrocarbyl group or optionally substituted sulphonated heterocyclyl group.

28. A process according to claim 27 wherein $R^{21}$ is a sulphonated phenyl group having n sulphonate groups where n is 1 to 5.

29. A process according to claim 27 or 28 wherein B is —$NH_2$ or —NH—.

30. A process according to claim 25 or 28 wherein E has 2, 3 or 4 carbon atoms linking A and B, said carbon atoms optionally carrying one or more substituents.

31. A process according to claim 30 wherein E is of the formula —$CHR^{30}$—$CHR^{31}$—where $R^{30}$ and $R^{31}$ are independently hydrogen or an optionally substituted hydrocarbyl group.

32. A process according to claim 30 wherein E has two carbon atoms linking A and B and is a bond in an optionally substituted cycloaliphatic ring.

33. A process according to claim 25 or 28 wherein $R^{18}$ is an optionally substituted aryl or an optionally substituted alkene.

34. A process according to claim 33 wherein $R^{18}$ is cymene.

35. A process according to claim 33 wherein $R^{18}$ is a pentamethylcyclopentadienyl group.

36. A process according to claim 25 or 28 wherein M is a group VIII transition metal.

37. A process according to claim 36 wherein M is ruthenium, rhodium or iridium.

38. A process according to claim 25 or 28 wherein the organic compound to be hydrogenated is a ketone, an amine or an iminium salt.

39. A process as claimed in claim 25 or 28 wherein the organic compound to be hydrogenated is of formula (I):

wherein:

X represents O, S, $CR^3R^4$, $NR^5$, $(NR^6R^7)^+Q^{31}$, $N^+R^8$—$O^-$, $(NR^9OR^{10})^+Q^-$, $NNR^{12}R^{13}$, $NNR^{12}SO_2R^{16}$, $NNR^{12}COR^{17}$, $(NR^{11}NR^{12}R^{13})^+Q^{31}$, $(NR^{11}NR^{12}C(=NR^{14})R^{15})^+Q^-$, $(NR^{11}NR^{12}SO_2R^{16})^+Q^-$, $(NR^{11}NR^{12}COR^{17})^+Q^-$, $NP(O)R^{15}R^{16}$, $NS(O)R^{15}$ or $NSO_2R^{15}$, $Q^-$ represents a monovalent anion;

$R^1$, $R^2$, $R^3$, $R^4$, $R^5$, $R^6$, $R^7$, $R^8$, $R^9$, $R^{10}$, $R^{11}$ $R^{12}$, $R^{13}$ and $R^{14}$ each independently represents a hydrogen atom, an optionally substituted hydrocarbyl, a perhalogenated hydrocarbyl or an optionally substituted heterocyclyl group, one or more of $R^1$ and $R^2$, $R^1$ and $R^3$, $R^1$ and $R^5$, $R^1$ and $R^6$, $R^1$ and $R^8$, $R^1$ and $R^9$, $R^1$ and $R^{11}$, $R^1$ and $R^{11}$, $R^1$ and $R^{12}$, $R^2$ and $R^4$, $R^2$ and $R^7$, $R^2$ and $R^{10}$, $R^3$ and $R^4$, $R^6$ and $R^7$, $R^9$ and $R^{10}$, $R^{11}$ and $R^{12}$, and $R^{12}$ and $R^{13}$ optionally being linked in such a way as to form an optionally substituted ring(s); and $R^{15}$, $R^{16}$ and $R^{17}$ each independently represents an optionally substituted hydrocarbyl, a perhalogenated hydrocarbyl or an optionally substituted heterocyclyl group.

40. A process as claimed in claim 25 or 28 wherein the organic compound to be hydrogenated is prochiral and the catalyst is chiral, an enatiomerically and/or diastereomerically purified form of the catalyst being employed, whereby the organic compound is asymmetrically hydrogenated.

41. A process according to claim 40 in which A—E—B comprises at least one stereo specific centre.

42. A process according to claim 25 or 28 in which the hydrogen donor is selected from hydrogen, primary and secondary alcohols, primary and secondary amines, carboxylic acids and their esters and amine salts, readily dehydrogenatable hydrocarbons, clean reducing agents, and any combination thereof.

43. A process according to claim 42 wherein the hydrogen donor is isopropanol.

44. A process according to claim 25 or 28 wherein the process is carried out in the presence of a base having $pK_a$ of at least 8.0.

45. A process as claimed in claim 25 or 28 wherein the catalyst is used in the form a supported liquid phase catalyst.

46. A process as claimed in claim 25 or 28 which comprises an additional step of adding an ion exchange resin after reacting the organic compound with the hydrogen donor in the presence of the catalyst.

47. A process according to claim 22 wherein $R^{33}$ and $R^{34}$ are independently phenyl or $R^{33}$ and $R^{34}$ are linked so as to define a cyclohexyl ring.

48. A process according to claim 24 wherein the oxidant is a mixture of sodium hydroxide solution and hydrogen peroxide solution.

* * * * *